US007964712B2

(12) United States Patent
Prussak et al.

(10) Patent No.: US 7,964,712 B2
(45) Date of Patent: *Jun. 21, 2011

(54) CHIMERIC NUCLEIC ACIDS ENCODING POLYPEPTIDES COMPRISING TNF ALPHA, CD70 AND FAS LIGAND DOMAINS

(75) Inventors: Charles E. Prussak, San Diego, CA (US); Thomas J. Kipps, Rancho Santa Fe, CA (US); Mark J. Cantwell, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/871,807

(22) Filed: Aug. 30, 2010

(65) Prior Publication Data

US 2011/0008842 A1    Jan. 13, 2011

Related U.S. Application Data

(62) Division of application No. 10/006,305, filed on Dec. 6, 2001, now Pat. No. 7,786,282.

(51) Int. Cl.
*C12N 15/62* (2006.01)
*C12N 15/12* (2006.01)
*C12N 15/00* (2006.01)
*C12N 15/63* (2006.01)

(52) U.S. Cl. ........... 536/23.4; 536/23.1; 536/23.5; 435/252.3; 435/320.1; 435/455

(58) Field of Classification Search .............. None
See application file for complete search history.

(56) References Cited

U.S. PATENT DOCUMENTS

| | | | |
|---|---|---|---|
| 4,990,455 A | 2/1991 | Yamagishi et al. | |
| 5,422,104 A | 6/1995 | Fiers et al. | |
| 5,480,981 A | 1/1996 | Goodwin et al. | |
| 5,486,463 A | 1/1996 | Lesslauer et al. | |
| 5,519,119 A | 5/1996 | Yamada et al. | |
| 5,540,926 A | 7/1996 | Aruffo et al. | |
| 5,565,321 A | 10/1996 | Spriggs et al. | |
| 5,573,924 A | 11/1996 | Beckmann et al. | |
| 5,606,023 A | 2/1997 | Chen et al. | |
| 5,716,805 A | 2/1998 | Srinivasan et al. | |
| 5,817,516 A | 10/1998 | Kehry et al. | |
| 5,861,310 A | 1/1999 | Freeman et al. | |
| 5,962,406 A | 10/1999 | Armitage et al. | |
| 6,017,527 A | 1/2000 | Maraskovsky et al. | |
| 6,106,832 A | 8/2000 | Spriggs et al. | |
| 6,451,759 B1 | 9/2002 | Kang et al. | |
| 6,544,523 B1 | 4/2003 | Chu | |
| 7,070,771 B1 | 7/2006 | Kipps et al. | |
| 7,495,090 B2 | 2/2009 | Prussak et al. | |
| 7,524,944 B2* | 4/2009 | Kipps et al. | 536/23.4 |
| 7,786,282 B2* | 8/2010 | Prussak et al. | 536/23.4 |
| 2002/0022017 A1 | 2/2002 | Yu | |
| 2004/0209295 A1 | 10/2004 | Schwabe et al. | |
| 2005/0158831 A1 | 7/2005 | Kornbluth | |

FOREIGN PATENT DOCUMENTS

| | | |
|---|---|---|
| EP | 0317641 | 5/1989 |
| EP | 0585943 | 3/1993 |
| EP | 0675200 | 10/1995 |
| EP | 1016721 | 7/2000 |
| WO | WO 91/02540 | 3/1991 |
| WO | WO 93/08207 | 4/1993 |
| WO | WO 93/19777 | 10/1993 |
| WO | WO 93/24135 | 12/1993 |
| WO | WO 94/04570 | 3/1994 |
| WO | WO 94/04680 | 3/1994 |
| WO | WO 94/17196 | 8/1994 |
| WO | WO 95/14487 | 6/1995 |
| WO | WO 95/17202 | 6/1995 |
| WO | WO 95/18819 | 7/1995 |
| WO | WO 95/32627 | 12/1995 |
| WO | WO 96/03141 | 2/1996 |
| WO | WO 96/14876 | 5/1996 |
| WO | WO 96/18413 | 6/1996 |
| WO | WO 96/22370 | 7/1996 |
| WO | WO 98/21232 | 5/1998 |
| WO | WO 98/26061 | 6/1998 |

OTHER PUBLICATIONS

Addison et al., "Intratumoral injection of an adenovirus expressing interleukin 2 induces regression and immunity in a murine breast cancer model," Proc. Natl. Acad. Sci. U.S.A., 92:8522-8526 (1995).
Alderson et al., "CD40 expression by human monocytes: Regulation by cytokines and activation of monocytes by the ligand for CD40." J. Exp. Med. 178: 669-674 (1993).
Ali et al., "PCR-Ligation-PCR Mutagenesis: A Protocol for Creating Gene Fusions and Mutations", BioTechniques, 18:746-750 (1995).
Ali et al., "The use of DNA viruses as vectors for gene therapy", Gene Therapy, 1:367-384(1994).
Armitage et al., "CD40 ligand is a T cell growth factor." Eur. J. Immunol., 23:2326-2331, 1993.
Armitage et al., "Molecular and biological characterization of a murine ligand for CD40", Nature, 357:80-82 (1992).

(Continued)

*Primary Examiner* — Phillip Gambel
(74) *Attorney, Agent, or Firm* — DLA Piper LLP (US)

(57) ABSTRACT

The present invention is directed to an isolated polynucleotide sequence encoding a chimeric TNFα, comprising a first nucleotide sequence encoding a domain or subdomain of a tumor necrosis factor ligand other than TNFα, wherein the encoded domain or subdomain replaces a cleavage site of native TNFα, and a second nucleotide sequence encoding a domain or subdomain of native TNFα that binds to a TNFα receptor. The encoded chimeric TNFα is significantly less susceptible to cleavage from the cellular surface and, as a result can increase the concentration of a ligand capable of binding to a TNFα receptor on the surface of a cell. The chimeric TNFα is therefore useful in methods for inducing apoptosis of a cell expressing a TNFα receptor, inducing activation of an immune system cell and treating neoplastic cells, by introducing into the cell of interest an isolated polynucleotide sequence encoding a chimeric TNFα that is expressed on the surface of the cell.

26 Claims, 10 Drawing Sheets

OTHER PUBLICATIONS

Aruffo et al., "The CD40 ligand, gp39, is defective in activated T cells from patients with X-linked hyper-Igfvl syndrome." Cell, 72:291-300,1993.

Attwood, "The Babel of Bioinformatics," Science 290:471-473 (2000).

Banchereau et al., "Long-Term Human B Cell Lines Dependent on Interleukin-4 and Antibody to CD40," Science, 251:70-72 (1991).

Banchereau et al., "The CD40 antigen and its ligand." Annual Review Immunol., 12:881-922,1994.

Berman et al., "Gene transfer in lymphoid cells: Expression of the Thy-1,2 antigen by Thy-1.1 BW5147 lymphoma cells transfected with unfractionated cellular DNA", Proc. Natl. Acad. Sci. USA, 81:7176-7179 (1984).

Blieden et al., "Class-I MHC Expression in the Mouse Lung Carcinoma, Line 1: A Model for Class-I Inducible Tumors", Int. J. Cancer Supp., 6:82-89 (1991).

Boles et al., "A rapid and highly efficient method for PCR-based site-directed mutagenesis using only one new primer", Curr. Genet, 28:197-198 (1995).

Boris-Lawrie et al., "Recent advances in retrovirus vector technology", Current Opinion in Genetics and Development, 3:102-109 (1993).

Brody et al., "Adenovirus-mediated in Vivo Gene Transfer", Ann. N. Y. Acad. Sci., 716:90-103 (1994).

Cadwell et al., "Randomization of Genes by PCR Mutagenesis", PCR Methods and Applications, 2:28-33 (1992).

Cantwell et al., "Acquired CD40-ligand deficiency in chronic lymphocytic leukemia", Nature Medicine, 3:984-989 (1997).

Cantwell et al., "Adenovirus Vector Infection of Chronic Lymphocytic Leukemia B Cells", Blood, 88:4676-4683 (1996).

Cantwell et al., "CD95 and FAS-ligand expression and apoptosis in rheumatoid arthritis." Arthritis and Rheumatism, 39(9), suppl., p. 287 (1996).

Carter, Barrie J., "Adeno-associated virus vectors", Current Opinion in Biotechnology, 3:533-539(1992).

Castle et al., "Regulation of expression of the ligand for CD40 on T helper lymphocytes." J. Immunol., 151:1777-1788, 1993.

Clark et al., "Activation of human B cells mediated through two distinct cell surface differentiation antigens, Bp35 and Bp50", Proc. Natl. Acad. Sci. U.S.A., 83:4494-4498(1986).

Cooper, Mark J., "Noninfectious Gene Transfer and Expression Systems for Cancer Gene Therapy", Seminars in Oncology, 23:172-187 (1996).

Cosman et al., "Cloning, sequence and expression of human interleukin-2 receptor", Nature, 312:768-771 (1984).

Danko et al., "Direct gene transfer into muscle", Vaccine, 12:1499-1502 (1994).

Davis et al., "Direct Gene Transfer into Skeletal Muscle in Vivo: Factors Affecting Efficiency of Transfer and Stability of Expression", Human Gene Therapy, 4:151-159(1993).

Deans et al., "Expression of an immunoglobulin heavy chain gene transfected into lymphocytes", Proc. Natl. Acad. Sci. USA, 81:1292-1296 (1984).

DeMatteo et al., "Gene Transfer to the Thymus", Annals of Surgery, 222:229-242(1995).

Dilloo, Dagmaretal., "CD40 Ligand Induces an Antileukemia Immune Response in Vivo", Blood, 90:1927-1933 (1997).

Evans et al., "Clinical Trial to Assess the Safety, Feasibility, and Efficacy of Transferring a Potentially Anti-Arthritic Cytokine Gene to Human Joints with Rheumatoid Arthritis", Human Gene Therapy, 7:1261-1280 (1996).

Fanslow et al., "Structural characteristics of CD40 ligand that determine biological function", Seminars in Immunology, 6:267-278 (1994).

Feigner et al., "Improved Cationic Lipid Formulations for in Vivo Gene Therapy", Ann. N. Y. Acad. Sci., 772:126-139 (1995).

Fisher et al., "In vivo and ex vivo gene transfer to the brain", Current Opinion in Neurobiology, 4:735-741 (1994).

Flotte et al., "Adeno-associated virus vectors for gene therapy", Gene Therapy, 2:357-362(1995).

Furth et al., "Gene Transfer into Mammalian Cells by Jet Injection", Hybridoma, 14:149-152(1995).

Galle et al., "Involvement of the CD95 (APO-1/Fas) Receptor and Ligand in Liver Damage", J. Exp. Med., 182:1223-1230 (1995).

Glorioso et al., "Development and application of herpes simplex virus vectors for human gene therapy", Annu. Rev. Microbiol., 49:675-710 (1995).

Goldspiel et al., "Human gene therapy", Clinical Pharmacy, 12:488-505 (1993).

Graham et al., "Manipulation of Adenovirus Vectors", Methods in Molecular Biology, 7(11):109-128 (1991).

Grewal et al., "CD40 and CD154 in cell-mediated immunity." Annual Review of Immunology, 16:111-135, 1998.

Hengge et al., "Expression of Naked DNA in Human, Pig, and Mouse Skin", Journal of Clinical Investigation, 97:2911-2916 (1996).

Henkel et al., "Functional Analysis of Mutated cDNA Clones by Direct Use of PCR Products in in Vitro Transcription/Translation Reactions", Analytical Biochemistry, 214:351-352(1993).

Hermann et al., "Expression of a 32-kDa ligand for the CD40 antigen on activated human T lymphocytes." Eur. J. Immunol., 23:961-964, 1993.

Hirano et al., "Inhibition of human breast carcinoma growth by a soluable recombinant human CD40 ligand." Blood, 93: 2999-3007, 1999.

Hollenbaugh et al., "The human T cell antigen gp39, a member of the TNF gene family, is a ligand for the CD40 receptor: expression of a soluble form of gp39 with B cell co-stimulatory activity", The EMBO Journal, 11:4313-4321 (1992).

Horton, Robert M., "PCR-mediated Recombination and Mutagenesis", Molecular Biotechnology, 3:93-99 (1995).

Jolly, Douglas, "Viral vector systems for gene therapy", Cancer Gene Therapy, 1:51-64 (1994).

Kass-Eisler et al., "Prospects for Gene Therapy with Direct Injection of Polynucleotides", Ann. N. Y. Acad. Sci., 772:232-240 (1995).

Kato et al., "Adenovirus-mediated gene transfer of CD40-ligand induces autologous immune recognition of chronic lymphocytic leukemia B cells." BLOOD, 90(10): p. 1157(1997).

Kato et al., "Gene transfer of C40-ligand induces autologous immune recognition of chronic lymphocytic leukemia B cells." J.Clin. Invest., 101:1133-1141, 1998.

Kikuchi et al., "Anti-tumor immunity induced by in vivo adenovirus vector-mediated expression of CD40 ligand in tumor cells." Hum. Gene Then, 10:1375-1387,1999.

Kipps et al., "New developments in flow cytometric analyses of lymphocyte markers", Laboratory Immunology II, 12:237-275 (1992).

Koc et al., "Transfer of Drug Resistance Genes Into Hematopoietic Progenitors to Improve Chemotherapy Tolerance", Seminars in Oncology, 23:46-65 (1996).

Kohn, Donald B., "The current status of gene therapy using hematopoietic stem cell", Current Opinion in Pediatrics, 7:56-63 (1995).

Korthauer et al., "Defective expression of T-cell CD40 ligand causes X-linked immunodeficiency with hyper-IgM" [see comments], Nature, 361:539-541, 1993.

Kouskoff et al., "Organ-Specific Disease Provoked by Systemic Autoimmunity", Cell, 87:811-822 (1997).

Kunkel et al., "Rapid and Efficient Site-Specific Mutagenesis without Phenotypic Selection", Methods in Enzymology, 154:367-382 (1987).

Kunkel, Thomas A., "Rapid and efficient site-specific mutagenesis without phenotypic selection", Proc. Natl. Acad. Sci. USA, 82:488-492 (1985).

Laman etal., "Functions of CD40 and its ligand, gp39 (CD40L)." Crit. Rev. Immunol., 16:59-108, 1996.

Lederman et al., T-BAM/CD40-L on helper T lymphocytes augments lymphokine-induced B cell Ig isotype switch recombination and rescues B cells from programmed cell death. Journal of Immunology 152:2163-2171 (1994).

Lu et al., "Stem cells from bone marrow, umbilical cord blood and peripheral blood for clinical application: current status and future application", Critical Reviews in Oncology/Hematology, 22:61-78 (1996).

Mackey et al., The role of CD40/CD154 interactions in the priming, differentiation, and effector function of helper and cytotoxic T cells. Journal of Leukocyte Biology, 63:418-428, 1998.

Majumder et al., "Background-minimized Cassette Mutagenesis by PCR Using Cassette-specific Selection Markers: A Useful General Approach for Studying Structure—Function Relationships of Multisubstrate Enzymes", PCR Methods and Applications, 4:212-218(1995).

Morris et al., "Incorporation of an isoleucine zipper motif enhances the biological activity of soluble CD40L (CD154)." The Journal of Biological Chemistry, 274:418-423, 1999.

Morrison et al., "A PCR-Based Strategy for Extensive Mutagenesis of a Target DNA Sequence", BioTechniques, 14:454-457 (1993).

Nadler, Lee M., "The Malignant Lymphomas", Harrison's Principles of Internal Medicine, Wilson et al., eds., McGraw-Hill, New York, Chapter 302, pp. 1599-1612, (2009).

Nagase et al., "Human Matrix Metalloproteinase Specificity Studies Using Collagen Sequence-Based Synthetic Peptides", Biopolymers (Peptide Science), 40:399-416 (1996).

Nakajima et al., "Antitumor effect of CD40 Ligand: elicitation of local systemic antitumor responses by IL-12 and B7." J. Immunol., 161:1901-1907, 1998.

Ngo, Thomas J. et al., "Computational Complexity, Protein Structure Prediction, and the Levinthal Paradox," The Protein Folding Problem and Tertiary Structure Prediction, Mertz et al. Editors, Birkhäuser Boston, pp. 491-495 (1994).

Okayama, Hiroto and Paul Berg, "A cDNA Cloning Vector That Permits Expression of cDNA Inserts in Mammalian Cells", Molecular and Cellular Biology, 3:280-289 (1983).

Peitsch et al., "A 3-D model for the CD40 ligand predicts that it is a compact trimer similar to the tumor necrosis factors", International Immunology, 5:233-238 (1993).

Pietravalle et al., "Cleavage of membrane-bound CD40 ligand is not required for inducing B cell proliferation and differentiation." Eur. J. Immunol., 26:725-7, 1996.

Prentice et al., "Ischemic/Reperfused Myocardium Can Express Recombinant Protein Following Direct DNA or Retroviral Injection", J. Mol. Cell Cardiol., 28:133-140 (1996).

Randrianarison-Jewtoukoff et al., "Recombinant Adenoviruses as Vaccines", Biologicals, 23:145-157 (1995).

Ranheim et al., "Activated T Cells Induce Expression of B7/BB1 on Normal or Leukemic B Cells through a CD40-dependent Signal", J. Exp. Med., 177:925-935 (1993).

Ranheim et al., "Tumor necrosis factor-alpha facilitates induction of CD80 (B7-1) and CD54 on human B cells by activated T cells: complex regulation by IL-4, IL-10, and CD40L." Cell Immunol. 161:226-235, 1995.

Raper et al., "Safety and Feasibility of Liver-Directed Ex Vivo Gene Therapy for Homozygous Familial Hypercholesterolemia", Annals of Surgery, 223:116-126 (1996).

Rassenti et al., "Lack of Allelic Exclusion in B Cell Chronic Lymphocytic Leukemia", J. Exp. Med., 185:1435-1445 (1992).

Raz et al., "Systemic immunological effects of cytokine genes injected into skeletal muscle", Proc. Natl. Acad. Sci. U.S.A., 90:4523-4527 (1993).

Roy et al., "The regulation of the expression of gp39, the CD40 ligand, on normal and cloned CD4+ cells." J. Immunol., 151:2497-2510, 1993.

Russell, S. J., "Replicating Vectors for Gene Therapy of Cancer: Risks, Limitations and Prospects", European Journal of Cancer, 30A:1165-1171 (1994).

Russell, Stephen J., "Replicating vectors for cancer therapy: a question of strategy", Seminars in Cancer Biology, 5:437-443 (1994).

Sambrook et al., "Standard Protocol for Calcium Phosphate-mediated Transfection of Adherent Cells", Molecular Cloning. A Laboratory Manual, 2d edition, Chapter 16:33-37 (1989).

Sato et al., "An aggressive nasal lymphoma accompanied by high levels of soluble Fas ligand", British Journal of Haematology, 94:379-382 (1996).

Schultze et al., "Autologous Tumor Infiltrating T Cells Cytotoxic for Follicular Lymphoma Cells Can Be Expanded in Vitro", Blood, 89:3806-3816 (1997).

Shaughnessy et al., "Parvoviral Vectors for the Gene Therapy of Cancer", Seminars in Oncology, 23:159-171 (1996).

Skolnick and Fetrow, "From genes to protein structure and function: novel applications of computational approaches in the genomic era." Trends in Biotechnology 18:34-39, (2000).

Smith et al., "Gene delivery systems for use in gene therapy: an overview of quality assurance and safety issues", Gene Therapy, 3:190-200 (1996).

Smith et al., "Rapid Identification of Highly Active and Selective Substrates for Stromelysin and Matrilysin Using Bacteriophage Peptide Display Libraries", The Journal of Biological Chemistry, 270:6440-6449 (1995).

Soubrane et al., "Direct Gene Transfer of a Plasmid Carrying the Herpes Simplex Virus—Thymidine Kinase Gene (HSV-TK) in Transplanted Murine Melanoma: In Vivo Study", European Journal of Cancer, 32A:691-695 (1996).

Spessot, Robert, "Cloning of the Herpes Simplex Virus ICP4 Gene in an Adenovirus Vector: Effects on Adenovirus Gene Expression and Replication", Virology, 168:378-387 (1989).

Srivastava, Arun, "Parvovirus-Based Vectors for Human Gene Therapy", Blood Cells, 20:531-538(1994).

Stappert et al., "A PCR method for introducing mutations into cloned DNA by joining an internal primer to a tagged flanking primer", Nucleic Acids Research, 20:624 (1992).

Sugaya et al., "Inhibition of Tumor Growth by Direct Intratumoral Gene Transfer of Herpes Simplex Virus Thymidine Kinase Gene with DNA-Liposome Complexes", Human Gene Therapy, 7:223-230 (1996).

Tesselaar et al., "Characterization of Murine CD70, the Ligand of the TNF Receptor Family Member CD27", The Journal of Immunology, 159:4959-4965 (1997).

Tessier et al., "PCR-Assisted Large Insertion/Deletion Mutagenesis", BioTechniques, 15:498-501 (1993).

Thomas et al., "Epstein-Barr Virus-Associated Lymphoproliferative Disorders in Immunocompromised Individuals", Advances in Cancer Research, Woude et al., eds., Academic Press, Inc., 57:329-380 (1991).

Tolstoshev, Paul, "Gene therapy, concepts, current trials and future directions", Annu. Rev. Pharmacol. Toxicol., 33:573-596 (1993).

Tracey et al., "Tumor Necrosis Factor: A Pleiotropic Cytokine and Therapuetic Tsic] Target", Annu. Rev. Med., 45:491-503 (1994).

Vallejo et al., "In Vitro Synthesis of Novel Genes: Mutagenesis and Recombination by PCR", PCR Methods and Applications, 4:S123-S130 (1994).

van Oers et al., "Expression and Release of CD27 in Human B-Cell Malignancies", Blood, 82:3430-3436 (1993).

Vilardaga et al., "Improved PCR Method for High-Efficiency Site-Directed Mutagenesis Using Class 2S Restriction Enzymes", BioTechniques, 18:604-606 (1995).

Vile et al., "Retroviruses as vectors", British Medical Bulletin, 51:12-30 (1995).

Vile et al., "Targeting of cytokine gene expression to malignant melanoma cells using tissue specific promoter sequences", Annals of Oncology, 5 Suppl. 4:S59-S65 (1994).

Wierda et al. "CD40-ligand (CD154) gene therapy for chronic lymphocytic leukemia." Blood, 96:2917-2924, 2000.

Wierda et al., "Infection of B-cell lymphoma with adenovirus vector encoding CD40-ligand (CD154) induces phenotypic changes that allow for autologous immune recognition."BLOOD, 90(15) 1997.

Wiley et al., "Exogenous CD40 Ligand Induces a Pulmonary Inflammation Response", Journal of Immunology, 158:2932-2938 (1997).

Woll et al., "Gene therapy for lung cancer", Annals of Oncology, 6 Suppl. 1:S73-S77 (1995).

Yee et al., "Generation of High-Tier Pseudotyped Retroviral Vectors with Very Broad Host Range", Methods in Cell Biology, Chapter 5,43:99-112 (1994).

Yellin et al., "T lymphocyte T Cell-B Cell-activating molecule/ CD4O-L molecules induce normal B Cells or chronic lymphocytic leukemia B cells to express CD80 (B7/BB-1) and enhance their costimulatory activity," J. Immun. 153:666-674 (1994).

Yovandich et al., "Gene Transfer to Synovial Cells by Intra-Articular Administration of Plasmid DNA", Human Gene Therapy, 6:603-610 (1995).

Zhang et al., "Amelioration of Collagen-induced Arthritis by CD95 (Apo-1/Fas)-ligand Gene Transfer", J. Clin. Invest, 100:1951-1957 (1997).

Cantwell et al., Membrane-Stabilized Chimeric Tumor Mecrosis Factor for Gene Therapy of B Cell Malignancies; (2001) BLOOD vol. 98 No. 11 Part 1, p. 423a, XP002315881 (Abstract).

Muller et al., (1999) Noncleavable Transmembrane Mouse Tumor Necrosis Factor-α (TNFα) Mediates Effects Distinct from Those of Wild-type TNFα in Vitro and in Vivo; J. of Biological Chemistry 274:53, 38112-38118.

Tang et al., "Length of the linking domain of human pro-tumor necrosis factor determines the cleavage processing." Biochemistry, 35:8226-8233, 1996.

Decoster et al., "Generation and biological characterization of membrane-bound, uncleavable murine tumor necrosis factor." The Journal of Biological Chemistry, 270(31): 18473-18478, 1995.

Moss et al., "Cloning of a disintegrin metalloproteinase that processes precursor tumour-necrosis factor-α." Nature, 385: 733-738, 1997.

Black et al., "A metalloproteinase disintegrin that releases tumour-necrosis factor-α from cells." Nature, 385:728-732, 1997.

International Search Report from application PCT/US02/39245, (mailed Oct. 22, 2003).

Perez et al., "Nonsecretable cell surface mutant of tumor necrosis factor TNF kills by cell-to-cell contact," CELL, 63(2):251-258(1990).

Cantwell, Mark J. et al., "Membrane-Stabilized Chimeric Tumor Necrosis Factor for Gene Therapy or B Cell Malignancies", *43rd Annual Meeting of the American Society of Hematology*, Dec. 2001.

\* cited by examiner

DOMAINS: I – CYTOPLASMIC DOMAIN; II – TRANSMEMBRANE DOMAIN; III – PROXIMAL EXTRACELLULAR DOMAIN; IV – DISTAL EXTRACELLULAR DOMAIN (PUTATIVE SOLUBLE FORM)

US 7,964,712 B2

SEQUENCE LISTING

```
<160> NUMBER OF SEQ ID NOS: 8

<210> SEQ ID NO 1
<211> LENGTH: 771
<212> TYPE: DNA
<213> ORGANISM: Artificial Sequence
<220> FEATURE:
<223> OTHER INFORMATION: Description of Artificial Sequence: Chimeric
      DNA construct comprising Domain IV of hTNFa linked to Domains I,
      II, and III of hCD154

<400> SEQUENCE: 1
atgatcgaaa catacaacca aacttctccc cgatctgcgg ccactggact gcccatcagc     60
atgaaaattt ttatgtattt acttactgtt tttcttatca cccagatgat tgggtcagca    120 cttttgctg tgtatcttca tagaaggctg gacaagatag aagatgaaag gaatcttcat    180
gaagattttg tattcatgaa aacgatacag agatgcaaca caggagaaag atccttatcc    240
ttactgaact gtgaggagta taaagccag tttgaaggct tgtgaagga tataatgtta     300 aacaaagagg agacgaagaa agatgaggat cctgtagccc atgttgtagc aaaccctcaa     360 gctgagggc agctccagtg gctgaaccgc cgggccaatg ccctcctggc caatggcgtg    420
gagctgagag ataaccagct ggtggtgcca tcagagggcc tgtacctcat ctactcccag    480
gtcctcttca agggccaagg ctgccctcc acccatgtgc tcctcaccca caccatcagc    540
cgcatcgccg tctcctacca gaccaaggtc aacctcctct ctgccatcaa gagccctgc     600
```

| | |
|---|---|
| cagagggaga ccccagaggg ggctgaggcc aagccctggt atgagcccat ctatctggga | 660 |
| ggggtcttcc agctggagaa gggtgaccga ctcagcgctg agatcaatcg gcccgactat | 720 |
| ctcgactttg cggagtctgg gcaggtctac tttggaatca ttgctctgtg a | 771 |

<210> SEQ ID NO 2
<211> LENGTH: 580
<212> TYPE: DNA
<213> ORGANISM: Artificial Sequence
<220> FEATURE:
<223> OTHER INFORMATION: Description of Artificial Sequence: Chimeric
  DNA construct comprising Domain IV of hTNFa linked to Domains I,
  II, and III of hCD70

<400> SEQUENCE: 2

| | |
|---|---|
| atgccggagg agggttcggg ctgctcggtg cggcgcaggc cctatgggtg cgtcctgcgg | 60 |
| gctgctttgg tcccattggt cgcgggcttg gtgatctgcc tcgtggtgtg catccagcgc | 120 |
| ttcgcacagg ctgcggatcc tgtagcccat gttgtagcaa accctcaagc tgaggggcag | 180 |
| ctccagtggc tgaaccgccg ggccaatgcc ctcctggcca atggcgtgga gctgagagat | 240 |
| aaccagctgg tggtgccatc agagggcctg tacctcatct actcccaggt cctcttcaag | 300 |
| ggccaaggct gccccctcca ccatgtgctc ctcacccaca ccatcagccg catcgccgtc | 360 |
| tcctaccaga ccaaggtcaa cctcctctct gccatcaaga gccccgcca gagggagacc | 420 |
| ccagaggggg ctgaggccaa gccctggtat gagcccatct atctgggagg ggtcttccag | 480 |
| ctggagaagg gtgaccgact cagcgctgag atcaatcggc ccgactatct cgactttgcg | 540 |
| gagtctgggc aggtctactt tggaatcatc gctctgtgaa | 580 |

<210> SEQ ID NO 3
<211> LENGTH: 837
<212> TYPE: DNA
<213> ORGANISM: Artificial Sequence
<220> FEATURE:
<223> OTHER INFORMATION: Description of Artificial Sequence: Chimeric
  DNA construct comprising Domain IV of hTNFa linked to Domains I,
  II, III of hFasL

<400> SEQUENCE: 3

| | |
|---|---|
| atgcagcagc ccttcaatta cccatatccc cagatctact gggtggacag cagtgccagc | 60 |
| tctccctggg cccctccagg cacagttctt ccctgtccaa cctctgtgcc agaaggcct | 120 |
| ggtcaaagga ggccaccacc accaccgcca ccgccaccac taccacctcc gccgccgccg | 180 |
| ccaccactgc ctccactacc gctgccaccc tgaagaaga gggaaccca agcacaggc | 240 |
| ctgtgtctcc ttgtgatgtt tttcatggtt ctggttgcct tggtaggatt gggcctgggg | 300 |
| atgtttcagc tcttccacct acagaaggag ctggcagaac tccgagagtc taccagccag | 360 |
| atgcacacag catcatcttt ggagaagcaa gcggatcctg tagcccatgt tgtagcaaac | 420 |
| cctcaagctg aggggcagct ccagtggctg aaccgccggg ccaatgccct cctggccaat | 480 |
| ggcgtggagc tgagagataa ccagctggtg gtgccatcag agggcctgta cctcatctac | 540 |
| tcccaggtcc tcttcaaggg ccaaggctgc cccctccacc atgtgctcct cacccacacc | 600 |
| atcagccgca tcgccgtctc ctaccagacc aaggtcaacc tcctctctgc catcaagagc | 660 |
| ccctgccaga gggagacccc agaggggct gaggccaagc cctggtatga gcccatctat | 720 |
| ctgggagggg tcttccagct ggagaagggt gaccgactca gcgctgagat caatcggccc | 780 |
| gactatctcg actttgcgga gtctgggcag gtctactttg gaatcattgc tctgtga | 837 |

<210> SEQ ID NO 4

```
<211> LENGTH: 813
<212> TYPE: DNA
<213> ORGANISM: Artificial Sequence
<220> FEATURE:
<223> OTHER INFORMATION: Description of Artificial Sequence: Chimeric
      DNA construct comprising Domain IV of hTNFa linked to Domains I,
      II, and III of hTRAIL

<400> SEQUENCE: 4
atggctatga tggaggtcca gggggaccc agcctgggac agacctgcgt gctgatcgtg      60
atcttcacag tgctcctgca gtctctctgt gtggctgtaa cttacgtgta ctttaccaac    120
gagctgaagc agatgcagga caagtactcc aaaagtggca ttgcttgttt cttaaaagaa    180
gatgacagtt attgggaccc caatgacgaa gagagtatga acagcccctg ctggcaagtc    240
aagtggcaac tccgtcagct cgttagaaag atgattttga gaacctctga ggaaaccatt    300
tctacagttc aagaaaagca acaaaatatt tctcccctag tgagagaaag aggtcctcag    360
agagtagcgg atcctgtagc ccatgttgta gcaaaccctc aagctgaggg gcagctccag    420
tggctgaacc gccgggccaa tgccctcctg gccaatggcg tggagctgag agataaccag    480
ctggtggtgc catcagaggg cctgtacctc atctactccc aggtcctctt caagggccaa    540
ggctgccccc tccaccatgt gctcctcacc cacaccatca gccgcatcgc cgtctcctac    600
cagaccaagg tcaacctcct ctctgccatc aagagcccct gccagaggga gaccccagag    660
ggggctgagg ccaagccctg gtatgagccc atctatctgg aggggtcttc cagctggag    720 aagggtgacc gactcagcgc tgagatcaat cggcccgact atctcgactt tgcggagtct    780
gggcaggtct actttggaat cattgctctg tga                                813

<210> SEQ ID NO 5
<211> LENGTH: 256
<212> TYPE: PRT
<213> ORGANISM: Artificial Sequence
<220> FEATURE:
<223> OTHER INFORMATION: Description of Artificial Sequence: Chimeric
      TNFa polypeptide encoded by the DNA sequence of SEQ ID NO:1

<400> SEQUENCE: 5

Met Ile Glu Thr Tyr Asn Gln Thr Ser Pro Arg Ser Ala Ala Thr Gly
 1               5                  10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Val
           100                 105                 110

Ala His Val Val Ala Asn Pro Gln Ala Glu Gly Gln Leu Gln Trp Leu
       115                 120                 125

Asn Arg Arg Ala Asn Ala Leu Leu Ala Asn Gly Val Glu Leu Arg Asp
   130                 135                 140

Asn Gln Leu Val Val Pro Ser Glu Gly Leu Tyr Leu Ile Tyr Ser Gln
145                 150                 155                 160

Val Leu Phe Lys Gly Gln Gly Cys Pro Ser Thr His Val Leu Leu Thr
```

-continued

```
                165                 170                 175

His Thr Ile Ser Arg Ile Ala Val Ser Tyr Gln Thr Lys Val Asn Leu
            180                 185                 190

Leu Ser Ala Ile Lys Ser Pro Cys Gln Arg Glu Thr Pro Glu Gly Ala
        195                 200                 205

Glu Ala Lys Pro Trp Tyr Glu Pro Ile Tyr Leu Gly Gly Val Phe Gln
    210                 215                 220

Leu Glu Lys Gly Asp Arg Leu Ser Ala Glu Ile Asn Arg Pro Asp Tyr
225                 230                 235                 240

Leu Asp Phe Ala Glu Ser Gly Gln Val Tyr Phe Gly Ile Ile Ala Leu
                245                 250                 255

<210> SEQ ID NO 6
<211> LENGTH: 192
<212> TYPE: PRT
<213> ORGANISM: Artificial Sequence
<220> FEATURE:
<223> OTHER INFORMATION: Description of Artificial Sequence: Chimeric
      TBFa polypeptide encoded by the DNA sequence of SEQ ID NO:2

<400> SEQUENCE: 6

Met Pro Glu Glu Gly Ser Gly Cys Ser Val Arg Arg Arg Pro Tyr Gly
  1               5                  10                  15

Cys Val Leu Arg Ala Ala Leu Val Pro Leu Val Ala Gly Leu Val Ile
             20                  25                  30

Cys Leu Val Val Cys Ile Gln Arg Phe Ala Gln Ala Ala Asp Pro Val
         35                  40                  45

Ala His Val Val Ala Asn Pro Gln Ala Glu Gly Gln Leu Gln Trp Leu
     50                  55                  60

Asn Arg Arg Ala Asn Ala Leu Leu Ala Asn Gly Val Glu Leu Arg Asp
 65                  70                  75                  80

Asn Gln Leu Val Val Pro Ser Glu Gly Leu Tyr Leu Ile Tyr Ser Gln
                 85                  90                  95

Val Leu Phe Lys Gly Gln Gly Cys Pro Ser Thr His Val Leu Leu Thr
            100                 105                 110

His Thr Ile Ser Arg Ile Ala Val Ser Tyr Gln Thr Lys Val Asn Leu
        115                 120                 125

Leu Ser Ala Ile Lys Ser Pro Cys Gln Arg Glu Thr Pro Glu Gly Ala
    130                 135                 140

Glu Ala Lys Pro Trp Tyr Glu Pro Ile Tyr Leu Gly Gly Val Phe Gln
145                 150                 155                 160

Leu Glu Lys Gly Asp Arg Leu Ser Ala Glu Ile Asn Arg Pro Asp Tyr
                165                 170                 175

Leu Asp Phe Ala Glu Ser Gly Gln Val Tyr Phe Gly Ile Ile Ala Leu
            180                 185                 190

<210> SEQ ID NO 7
<211> LENGTH: 278
<212> TYPE: PRT
<213> ORGANISM: Artificial Sequence
<220> FEATURE:
<223> OTHER INFORMATION: Description of Artificial Sequence: Chimeric
      TNFa polypeptide encoded by the DNA sequence of SEQ ID NO:3

<400> SEQUENCE: 7
```

```
Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
             35                  40                  45

Pro Pro Pro Pro Pro Leu Pro Pro Pro Pro Pro Pro Pro Pro Leu Pro
         50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
             100                 105                 110

Glu Leu Arg Glu Ser Thr Ser Gln Met His Thr Ala Ser Ser Leu Glu
             115                 120                 125

Lys Gln Ala Asp Pro Val Ala His Val Val Ala Asn Pro Gln Ala Glu
             130                 135                 140

Gly Gln Leu Gln Trp Leu Asn Arg Arg Ala Asn Ala Leu Leu Ala Asn
145                 150                 155                 160

Gly Val Glu Leu Arg Asp Asn Glu Leu Val Val Pro Ser Glu Gly Leu
                 165                 170                 175

Tyr Leu Ile Tyr Ser Gln Val Leu Phe Lys Gly Gln Gly Cys Pro Ser
             180                 185                 190

Thr His Val Leu Leu Thr His Thr Ile Ser Arg Ile Ala Val Ser Tyr
             195                 200                 205

Gln Thr Lys Val Asn Leu Leu Ser Ala Ile Lys Ser Pro Cys Gln Arg
             210                 215                 220

Glu Thr Pro Glu Gly Ala Glu Ala Lys Pro Trp Tyr Glu Pro Ile Tyr
225                 230                 235                 240

Leu Gly Gly Val Phe Gln Leu Glu Lys Gly Asp Arg Leu Ser Ala Glu
                 245                 250                 255

Ile Asn Arg Pro Asp Tyr Leu Asp Phe Ala Glu Ser Gly Gln Val Tyr
             260                 265                 270

Phe Gly Ile Ile Ala Leu
             275

<210> SEQ ID NO 8
<211> LENGTH: 270
<212> TYPE: PRT
<213> ORGANISM: Artificial Sequence
<220> FEATURE:
<223> OTHER INFORMATION: Description of Artificial Sequence: Chimeric
      TNFa polypeptide encoded by the DNA sequence of SEQ ID NO:4

<400> SEQUENCE: 8

Met Ala Met Met Glu Val Gln Gly Gly Pro Ser Leu Gly Gln Thr Cys
  1               5                  10                  15

Val Leu Ile Val Ile Phe Thr Val Leu Leu Gln Ser Leu Cys Val Ala
             20                  25                  30

Val Thr Tyr Val Tyr Phe Thr Asn Glu Leu Lys Gln Met Gln Asp Lys
             35                  40                  45

Tyr Ser Lys Ser Gly Ile Ala Cys Phe Leu Lys Glu Asp Asp Ser Tyr
             50                  55                  60

Trp Asp Pro Asn Asp Glu Glu Ser Met Asn Ser Pro Cys Trp Gln Val
 65                  70                  75                  80
```

```
Lys Trp Gln Leu Arg Gln Leu Val Arg Lys Met Ile Leu Arg Thr Ser
             85                  90                  95

Glu Glu Thr Ile Ser Thr Val Gln Glu Lys Gln Gln Asn Ile Ser Pro
            100                 105                 110

Leu Val Arg Glu Arg Glu Pro Gln Arg Val Ala Asp Pro Val Ala His
            115                 120                 125

Val Val Ala Asn Pro Gln Ala Glu Gly Gln Leu Gln Trp Leu Asn Arg
        130                 135                 140

Arg Ala Asn Ala Leu Leu Ala Asn Gly Val Glu Leu Arg Asp Asn Gln
145                 150                 155                 160

Leu Val Val Pro Ser Glu Gly Leu Tyr Leu Ile Tyr Ser Gln Val Leu
                165                 170                 175

Phe Lys Gly Gln Gly Cys Pro Ser Thr His Val Leu Leu Thr His Thr
                180                 185                 190

Ile Ser Arg Ile Ala Val Ser Tyr Gln Thr Lys Val Asn Leu Leu Ser
            195                 200                 205

Ala Ile Lys Ser Pro Cys Gln Arg Glu Thr Pro Glu Gly Ala Glu Ala
        210                 215                 220

Lys Pro Trp Tyr Glu Pro Ile Tyr Leu Gly Gly Val Phe Gln Leu Glu
225                 230                 235                 240

Lys Gly Asp Arg Leu Ser Ala Glu Ile Asn Arg Pro Asp Tyr Leu Asp
                245                 250                 255

Phe Ala Glu Ser Gly Gln Val Tyr Phe Gly Ile Ile Ala Leu
                260                 265                 270
```

CHIMERIC NUCLEIC ACIDS ENCODING POLYPEPTIDES COMPRISING TNF ALPHA, CD70 AND FAS LIGAND DOMAINS

CROSS REFERENCE TO RELATED APPLICATIONS

This application is a divisional application of U.S. application Ser. No. 10/006,305 filed Dec. 6, 2001, now issued as U.S. Pat. No. 7,786,282. The disclosure of the prior application is considered part of and is incorporated by reference in the disclosure of this application.

TECHNICAL FIELD OF THE INVENTION

The present invention relates to the fields of biochemistry, immunology, genetic engineering, and medicine. In particular, it relates to novel chimeric ligands that, when expressed on the surface of a cell, are more stable than the corresponding native ligand.

BACKGROUND OF THE INVENTION

The immune system eliminates malignant cells by recognizing them as foreign and then clearing them from the body. To accomplish this, the immune system invokes both an antibody response and a cellular response. Both these responses require interaction among a number of different cells of the immune system (Abbas, Cellular and Molecular Immunology, 2000)

An immune reaction typically begins with a T lymphocyte (T cell) that has on its surface a T cell receptor (TCR) that binds to an antigen derived peptide associated with a class II major histo-compatability complex (MHC) molecule. The T cell also expresses on its surface various polypeptides, which are referred to as "ligands" because they bind to receptors on cells associated with an immune-mediated response, as described in more detail below. When the T cell receptor binds to a MHC-associated antigen, such as antigen derived from a malignant cell, it becomes activated and expresses a ligand on its surface. The ligand is only present on the cell surface for a short time, and once it has been removed from the surface of the cell, the T cell's ability to bind a receptor-bearing cell is lost. One such ligand is called tumor necrosis factor (TNFα).

TNFα, when expressed on the surface of an activated T cell, binds to receptors, such as TNF-receptor I (also known as "p55" or "CD120a") and TNF-receptor II (also known as "p75" or "CD120b"), expressed on the surface of immune cells, non-immune cells, and malignant cells. Included among these immune cells are cells collectively referred to as "antigen presenting cells" (APC) because they express surface polypeptides that are able to bind and present antigen to the T cell. Examples of APC include dendritic cells and B cells. APC also have various receptor molecules on their surfaces that interact with other cells of the immune system. The interaction between ligands expressed by T cells and receptor molecules on APC and malignant cells causes a cytolytic reaction that destroys the malignant cells and clears them from the body.

TNFα is one member of a larger family of ligands, collectively referred to as the TNF superfamily (Gruss et al, Cytokines Mol Ther, 1:75-105, 1995 and Locksley et al, Cell, 104: 487-501, 2001). Members of the TNF superfamily include Fas ligand ("FasL"), TNFα, LTα, lymphotoxin (TNFβ), CD154, TRAIL, CD70, CD30 ligand, 4-1BB ligand, APRIL, TWEAK, RANK ligand, LIGHT, AITR ligand, ectodysplasin, BLYS, VEGI, and OX40 ligand. TNF superfamily members share a conserved secondary structure comprising four domains: domain I, the intracellular domain; domain II, which spans the cell membrane and is known as the transmembrane domain; domain III, which consists of the extracellular amino acids closest to the cell membrane; and domain IV, the distal extracellular domain (Kipps et al., WO98/26061 published Jun. 18, 1998). Typically, at least a part of domain IV can be cleaved from the parent molecule. The cleaved fragment often exhibits the same biological activity of the intact ligand and is conventionally referred to as a "soluble form" of the TNF family member.

I. Biological Activity of TNFα.

There are two bioactive forms of TNFα. One form is membrane-integrated (mTNFα), also referred to as pro-TNFα. In addition, there is a soluble form (sTNFα) generated by proteolytic cleavage of mTNFα. TNF signals through two distinct receptors, CD120a and CD120b. In general, TNF signaling through CD120a induces cellular apoptosis due to the presence of a cytoplasmic death domain in CD120a. In contrast, CD120b, which lacks a death domain, generally induces cellular activation, such as proliferation and costimulatory molecule expression. These latter effects are highlighted in normal B cells in which TNFα induced expression of important costimulatory molecules, including CD80 and CD54 (Ranheim and Kipps, Cell Immunol. 161:226, 1995).

A matrix metalloproteinase (mmp) called TACE (for TNF-alpha converting enzyme) has been shown to release the soluble form of TNFα (Black et al, Nature, 385:729-733, 1997 and Moss et al, Nature, 385:733-736, 1997). TACE has been found to release sTNFα by cleaving pro-TNFα between amino acid residues alanine76 and valine77. Moreover, this cleavage is dependent on an approximately 12 amino acid mmp recognition sequence spanning valine77 to proline88 (Decoster et al, J Biol Chem, 270:18473-18478, 1995 and Tang et al, Biochemistry, 35:8226-8233, 1996) since deletion of 9 to 12 amino acids of this mmp recognition site inhibited the cleavage of the parent TNFα molecule (Decoster et al, J Biol Chem, 270:18473-18478, 1995 and Perez et al, Cell, 63:251-258, 1990). However, deletion of this cleavage site does not necessarily completely abrogate sTNFα generation due to the existence of multiple cleavage sites in TNFα (Mueller et al, J Biol Chem, 274:38112-38118, 1999).

II. Drawbacks of Current TNFα Constructs in Treating Human Diseases

Since TNFα can induce apoptosis of CD120a expressing cells as well as enhance immune responses by cellular activation through CD120b, groups attempted to use TNFα as an anti-tumor compound. However, immune therapy of most cancers with recombinant soluble TNFα showed little clinical efficacy due to the failure to achieve high local concentrations of cytokine without systemic toxicity. Common side effects include fever, chills, anorexia, hypertension, liver abnormalities, and hematological changes (Spriggs et al, Ciba Found Symp, 131:206-227, 1987). Moreover, gene transfer of even wild-type (wt) TNF, expressed as the membrane-associated pro-TNFα, cannot achieve high local expression of TNF without systemic toxicity since it is metabolized rapidly into a soluble cytokine. Since the soluble form of TNFα is the common factor for the failure of TNFα as a therapeutic compound, we hypothesized that design of membrane-stabilized TNFα might allow local delivery of TNFα while mitigating the risk of systemic toxicity associated with soluble TNFα.

Given the disadvantages of current TNFα applications, there is clearly a need for a membrane-stabilized TNFα that maintains the receptor binding function of native TNFα but that is less susceptible to cleavage and is thereby less likely to generate the soluble form of TNFα. The present invention provides such a membrane-stabilized TNFα ligand.

SUMMARY OF THE INVENTION

The present invention relates to novel chimeric TNFα that are more stable when expressed on the surface of cells than non-chimeric TNFα. These novel ligands are chimeric in that they are comprised of domains or subdomains of at least two different members of the TNF superfamily. Specifically, at least one domain or subdomain of TNF that contains a "cleavage site(s)" is replaced with a corresponding domain or subdomain of another ligand of the TNF superfamily, preferably CD154, CD70, FasL or TRAIL. In addition, the chimeric ligand is composed of a domain or subdomain of TNFα that is responsible for binding to the cognate TNFα receptors. The present invention also relates to novel polynucleotide sequences encoding chimeric TNFα, expression vectors comprising the novel polynucleotide sequences, and methods of producing the novel chimeric ligands. Finally, the present invention relates to methods of using the expression vectors to improve the immunoreactivity of transfected cells and to treat malignant tumors.

Thus, one aspect of this invention relates to an isolated polynucleotide sequence encoding a chimeric TNFα, comprising a first nucleotide sequence encoding a domain or subdomain of a tumor necrosis factor ligand other than TNFα, wherein the encoded domain or subdomain replaces a cleavage site of native TNFα, and a second nucleotide sequence encoding a domain or subdomain of native TNFα that binds to a TNFα receptor.

An aspect of this invention is the above isolated polynucleotide sequence wherein the first nucleotide sequence encodes domain II, or a subdomain of domain III, of the other tumor necrosis factor ligand.

An aspect of this invention is the above isolated polynucleotide sequence wherein the first nucleotide sequence additionally encodes domain II, or a subdomain of domain II, of the other tumor necrosis factor ligand.

An aspect of this invention is an isolated polynucleotide sequence such as those described above wherein the first nucleotide sequence additionally encodes domain I, or a subdomain of domain I, of the other tumor necrosis factor ligand.

An aspect of this invention is an isolated polynucleotide sequence such as those described above wherein the first nucleotide sequence additionally encodes a subdomain of domain IV of the other tumor necrosis factor ligand.

An aspect of this invention is an isolated polynucleotide sequence such as those described above, wherein the other tumor necrosis factor ligand is selected from the group consisting of CD154, CD70, Fas ligand and TRAIL.

An aspect of this invention is an isolated polynucleotide sequence such as those described above in which the second nucleotide sequence encodes domain IV, or a subdomain of domain IV, of native TNFα.

An aspect of this invention is an isolated polynucleotide sequence such as those described above in which the second nucleotide sequence encodes a subdomain of domain IV of native TMFα that leaves a cleavage site of native TNFα

An aspect of this invention is an isolated polynucleotide sequence such as those described above in which the first nucleotide sequence encodes domains I, II and III, or subdomains of one or more of domains I, II and III, of a tumor necrosis factor ligand selected from the group consisting of CD154, CD70, Fas ligand, and TRAIL and the second nucleotide sequence encodes domain IV, or a subdomain of domain IV, of native TNFα

An aspect of this invention is an isolated polynucleotide sequence such as those described above in which the first nucleotide sequence encodes domains I, II and III, or subdomains of one or more domains I, II and III, of CD154 and the second nucleotide sequence encodes domain IV, or a subdomain of domain IV, of native TNFα

An aspect of this invention is an isolated polynucleotide sequence such as those described above further comprising a linker domain encoding a peptide of at least one amino acid that links the first nucleotide sequence and the second nucleotide sequence.

An aspect of this invention is an isolated polynucleotide sequence such as those described above in which the sequence is selected from the group consisting of SEQ. ID. NO. 1, SEQ. ID. NO. 2, SEQ. ID. NO. 3 and SEQ. ID. NO. 4.

An aspect of this invention is an isolated polynucleotide sequence such as those F,;z described above in which the chimeric TNFα comprises an amino acid sequence selected from the group consisting of SEQ. ID. NO. 5, SEQ. ID. NO. 6, SEQ. ID. NO. 7 and SEQ. ID. NO. 8.

An aspect of this invention is a chimeric TNFα comprising a first domain or subdomain of a tumor necrosis factor ligand other than TNFα, wherein the domain or subdomain replaces a cleavage site of native TNFα, and a second domain or subdomain of native TNFα that binds to a TNFα receptor.

An aspect of this invention is a chimeric TNFα that is less susceptible to cleavage from the surface of cells than native TNFα.

An aspect of this invention is a chimeric TNFα having a cleavage rate that is approximately 90% less than that of native TNFα ligand.

An aspect of this invention is a chimeric TNFα such as those described above in which the domain or subdomain comprises domain III, or a subdomain of domain III, of the other tumor necrosis factor ligand.

An aspect of this invention is a chimeric TNFα such as those described above in which the domain or subdomain further comprises domain II, or a subdomain of domain II, of the other tumor necrosis factor ligand.

An aspect of this invention is a chimeric TNFα such as those described above in which the domain or subdomain further comprises domain I, or a subdomain of domain I, of the other tumor necrosis factor ligand.

An aspect of this invention is a chimeric TNFα such as those described above in which the domain or subdomain further comprises a subdomain of domain IV of the other tumor necrosis factor ligand.

An aspect of this invention is a chimeric TNFα such as those described above in which the other tumor necrosis factor ligand is selected from the group consisting of CD154, CD70, Fas ligand and TRAIL.

An aspect of this invention is a chimeric TNFα such as those described above further comprising domain IV, or a subdomain of domain IV, of native TNFα.

An aspect of this invention is a chimeric TNFα such as those described above comprising a subdomain of domain IV of native TNFα that lacks a cleavage site of native TNFα.

An aspect of this invention is a chimeric TNFα such as those described above comprising domains I, II and III, or subdomains of one or more of domains I, II and III, of a tumor necrosis factor ligand selected from the group consisting of CD154, CD70, Fas ligand and TRAIL, and domain IV, or a subdomain of domain IV, of native TNFα.

An aspect of this invention is a chimeric TNFα such as those described above comprising domain I, domain II and domain III, or subdomains of one or more domains I, II and III, of CD154 and domain IV, of a subdomain of domain IV, of native TNFα

An aspect of this invention is a chimeric TNFα such as those described above additionally comprising a linker domain that links the first domain or subdomain to the second domain or subdomain.

An aspect of this invention is an expression vector comprising one of the above isolated polynucleotide sequences.

An aspect of this invention is the above expression vector in which the polynucleotide sequence encodes a chimeric TNFα comprising domain III, or a subdomain of domain III, of a tumor necrosis factor ligand selected from the group consisting of CD154, CD70, Fas ligand and TRAIL, and domain IV, or a subdomain of domain IV, of native TNFα

An aspect of this invention is an expression vector such as those described above further comprising a polynucleotide sequence that encodes domain II, or a subdomain of domain II, of a tumor necrosis factor ligand selected from the group consisting of CD154, CD70, Fas ligand and TRAIL.

An aspect of this invention is an expression vector such as those described above further comprising a polynucleotide sequence that encodes domain I, or a subdomain of domain I, of a tumor necrosis factor ligand selected from the group consisting of CD154, CD70, Fas ligand and TRAIL.

An aspect of this invention is an expression vector such as those described above further comprising a polynucleotide sequence that encodes a subdomain of domain IV of a tumor necrosis factor ligand selected from the group consisting of CD154, CD70, Fas ligand and TRAIL.

An aspect of this invention is an expression vector such as those described above further comprising a polynucleotide sequence that encodes a subdomain of domain IV of a tumor necrosis factor ligand selected from the group consisting of CD154, CD70, Fas ligand and TRAIL.

An aspect of this invention is an expression vector such as those described above further comprising viral DNA or bacterial DNA.

An aspect of this invention is an expression vector such as those described above further comprising adenoviral DNA, retroviral DNA, or other viral gene transfer system.

An aspect of this invention is an expression vector such as those described above further comprising a promoter region.

An aspect of this invention is an expression vector such as those described above further comprising a polyadenylation signal region.

An aspect of this invention is a genetic construct comprising one of the isolated polynucleotide sequences described above operatively linked to a promoter sequence and to a polyadenylation signal sequence.

An aspect of this invention is a host cell comprising one of the expression vectors or genetic constructs described above.

The above host cell is a mammalian cell in an aspect of this invention.

The host cell is an antigen presenting cell in an aspect of this invention.

The host cell is a tumor cell in an aspect of this invention.

An aspect of this invention is a process for producing a chimeric TNFα comprising culturing one of the above host cells under conditions suitable to effect expression of the protein.

An aspect of this invention is a method for increasing the concentration of a ligand capable of binding to a TNFα receptor on the surface of a cell, comprising introducing into the cell an isolated polynucleotide sequence encoding a chimeric TNFα whereby the chimeric TNFα is less susceptible to cleavage from the surface of the cells than native TNFα.

An aspect of this invention is the above method in which the isolated polynucleotide sequence comprises one of the expression vectors or genetic constructs described above.

An aspect of this invention is the above method in which the cell is a mammalian cell.

An aspect of this invention is the above method in which the cell expresses a TNFα receptor on its surface.

An aspect of this invention is a method for inducing apoptosis in a cell expressing a TNFα receptor comprising introducing into the cell an isolated polynucleotide sequence encoding a chimeric TNFα that is expressed on the surface of the cell.

An aspect of this invention is a method for inducing the activation of an immune system cell comprising introducing into the cell an isolated polynucleotide sequence encoding a chimeric TNFα that is expressed on the surface of the cell.

An aspect of this invention is a method for treating neoplasia in a patient comprising introducing into a neoplastic cell an isolated polynucleotide sequence encoding a chimeric TNFα that is expressed on the surface of the cell.

An aspect of this invention is the above method further comprising obtaining the neoplastic cell from a human patient and infusing the neoplastic cell back into the patient after having introduced into the cells a polynucleotide sequence encoding a chimeric TNFα.

An aspect of this invention is a method of treating neoplasia comprising injecting into a tumor bed of a patient an isolated polynucleotide sequence encoding a chimeric TNFα that is then expressed on the surface of the cells.

DETAILED DESCRIPTION OF THE INVENTION

Figure 1:
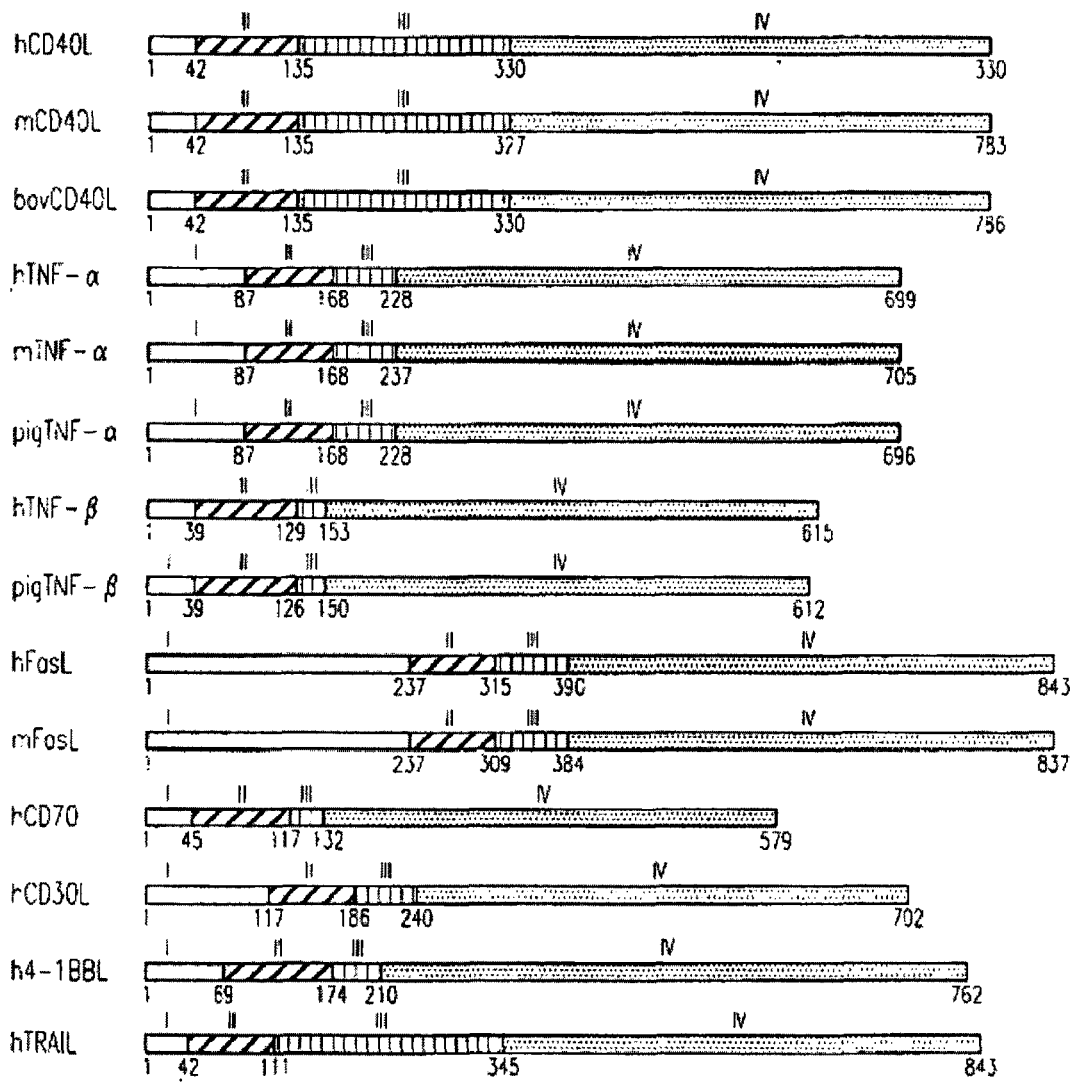
FIG. 1 is a schematic diagram of a number of human and mouse ligands of the TNF superfamily depicting domains I-IV of those ligands (Kipps et al., WO98/26061 published Jun. 18, 1998).

All cited references are incorporated by reference, including any drawings, as if fully set forth herein.

I. Definitions

As used herein, the term "chimeric TNFα" refers to a ligand comprised of at least one domain or subdomain of TNFα and at least one domain or subdomain of another TNF ligand other than TNFα.

As used herein, the term "subdomain" refers to a sequence of at least two amino acids that is part of a domain of a TNF ligand. A "subdomain" also encompasses an amino acid sequence from which one or more amino acids have been deleted, including one or more amino acids truncated from an end of the sequence.

As used herein, the term "cleavage site" and "mmp recognition site" refer to a sequence of amino acids that is recognized by proteases, typically matrix metalloproteases (mmp), such as TNFα converting enzyme (TACE), that cleave TNFα from the surface of the expressing cell. TACE has been found to release sTNFα by cleaving pro-TNF between amino acid residues alanine76 and valine77. Moreover, this cleavage is dependent on an approximately 12 amino acid mmp recognition sequence spanning valine77 to proline88. The cleavage site of TNFα is typically found at or around the boundaries of domains III and IV of TNFα

As used herein, the term "linker domain" refers to a sequence of at least one amino acid that is not part of the native TNFα ligand that joins a domain or subdomain of TNFα chimeric constructs. Although the linker domain is typically two to four amino acids in length as described in our examples, the linker can be any number of amino acids (one amino acid and greater) as long as it does not affect the binding of TNFα chimeric constructs to its cognate receptors. This linker can be composed of noncharged (e.g. alanine and glycine) or charged amino acids (e.g. aspartic acid). Moreover, the linker domain is not an absolute requirement in chimeric TNFα constructs since removal of the linker domain should not affect the function or metabolic processing of the TNFα chimeras. The use of linker domains is described in the literature (Ladurner et al, J Mol Biol, 273:330-337, 1997 and Wu et al, Q J Nucl Med, 44:268-283, 2000).

As used herein, the phrase "less susceptible to cleavage" refers to the higher resistance of a chimeric TNFα to proteolytic cleavage compared to that of native TNFα, as measured by the amount of soluble TNF generated by a given number of cells over a period of time. Thus, a chimeric TNFα of the present invention is "less susceptible to cleavage" because it is cleaved at a rate preferably at least 90% less than that of native TNFα

As used herein, the term "expression vector" refers to a nucleic acid that expresses a recombinant nucleotide sequence and that is capable of infecting cells and replicating itself therein. Typical expression vectors include plasmids used in recombinant DNA technology and various viruses capable of replicating within bacterial or animal cells. A number of expression vectors have been described in the literature. Cantwell et al., Blood, In (1996) entitled "Adenovirus Vector Infection of Chronic Lymphocytic Leukemia B Cells;" Woll, P. J. and I. R. Hart, Ann. Oncol., 6 Suppl 1:73 (1995); Smith, K. T., A. J. Shepherd, J. E. Boyd, and G. M. Lees, Gene Ther., 3:190 (1996); Cooper, M. J., Semin. Oncol., 23:172 (1996); Shaughnessy, E. D. Lu, S. Chatterjee, and K. K. Wong, Semin. Oncol., 23:159 (1996); Glorioso, J. C., N. A. DeLuca, and D. J. Fink, Annu. Rev. Microbiol., 49:675 (1995); Flotte, T. R. and B. J. Carter, Gene Ther., 2:357 (1995); Randrianarison-jewtoukoff, V. and M. Perricaudet, Biologicals., 23:145 (1995); Kohn, D. B., Curr. Oin. Pediatr., 7:56 (1995); Vile, R. G. and S. J. Russell, Br. Med. Bull., 51:12 (1995); Russell, S. J., Semin. Cancer Biol., 5:437 (1994); and Ali, M., N. R. Lemoine, and C. J. Ring, Gene Ther., 1:367 (1994).

II. Chimeric DNA Sequences Encoding Chimeric TNFα Ligand

As noted above, ligands of the TNF superfamily ("TNF ligands") have a similar secondary structure consisting of a number of domains (Kipps et al., WO98/76061 published Jun. 18, 1998). In Table I, the domain boundaries of a number of ligands of the TNF superfamily are shown. Based on the x-ray crystal structure of human TNFα, the predicted secondary structure of the receptor-binding portion of CD40 ligand has been deduced (Peitsch et al, Int Immunol, 5:233-238, 1993). The secondary structures of the receptor-binding portions of other TNF ligands were deduced by comparison to human TNFα, using computer analysis.

TABLE I

DOMAIN STRUCTURE OF LIGANDS FROM THE TNF SUPERFAMILY*

|  | Domain I (Cytoplasmic) | Domain II (Transmembrane) | Domain III (Proximal Extracellular) | Domain IV (Distal Extracellular) |
|---|---|---|---|---|
| Human CD154 | 1-42 | 42-135 | 135-330 | 330-786 |
| Murine CD154 | 1-42 | 42-135 | 135-327 | 327-783 |
| Bovine CD154 | 1-42 | 42-135 | 135-330 | 330-786 |
| Human TNFα | 1-87 | 87-168 | 168-228 | 228-699 |
| Murine TNFα | 1-87 | 87-168 | 168-237 | 237-705 |

TABLE I-continued

DOMAIN STRUCTURE OF LIGANDS FROM
THE TNF SUPERFAMILY*

|  | Domain I (Cytoplasmic) | Domain II (Transmembrane) | Domain III (Proximal Extracellular) | Domain IV (Distal Extracellular) |
|---|---|---|---|---|
| Porcine TNFα | 1-87 | 87-168 | 168-228 | 228-696 |
| Human Fas Ligand | 1-237 | 237-315 | 315-390 | 390-843 |
| Murine Fas Ligand | 1-237 | 237-309 | 309-384 | 384-837 |
| Human CD70 | 1-45 | 45-117 | 117-132 | 132-579 |
| Human CD30 Ligand | 1-117 | 117-186 | 186-240 | 240-702 |
| Human TRAIL | 1-42 | 42-111 | 111-345 | 345-843 |

*The domains are identified by the nucleotide boundaries of each domain using the first nucleotide of the initial methionine of the cDNA as nucleotide number 1. According to the invention, the nucleotide boundaries shown may vary considerably from those identified and still define domains that are useful in the present invention.

Given the similarity of structure among TNF superfamily members and the nucleotide sequences coding for them, a nucleotide sequence encoding one domain or subdomain from TNFα should be interchangeable with the corresponding nucleotide sequence of another TNF ligand to result in a hybrid polynucleotide sequence that encodes a chimeric TNFα.

The nucleotide sequences that are exchanged for corresponding sequences in a different TNF ligand gene are selected for functional reasons, i.e., because the new sequence encodes a domain or subdomain that either provides or modifies a desired function, or eliminates an undesired function of the target ligand gene. For example, it is well known that at least part of TNFα is cleaved from the parent molecule and becomes a soluble form. As noted above, the soluble form is generally undesirable. Thus, exchanging a sequence from a TNF ligand that does not contain a cleavage with the cleavage site(s) of TNFα that give rise to the soluble form of TNFα would at least partially ameliorate that problem.

According to the invention, domain III of TNFα includes sequences of amino acids that are cleaved by proteases. For instance, cleavage sites have been identified for TNFα between amino acids ALA76 and VAL77. Cleavage at this site generates a soluble form of the TNFα molecule. As noted above, native TNFα may have additional cleavage sites in domains I-IV (Mueller et al, J Biol Chem, 274:38112-38118, 1999).

Moreover, according to the invention, domain IV of TNFα includes one or more amino acids that are necessary in binding to TNFα receptors and must be conserved to maintain TNFα receptor binding.

Thus, a presently preferred embodiment of the present invention is a chimeric TNFα polynucleotide sequence comprising a first nucleotide sequence encoding a domain or subdomain of a TNF ligand other than native TNFα, wherein the encoded domain or subdomain replaces the domain or subdomain of native TNFα that contains a cleavage site. Thus, this first sequence may, without limitation, encode any of the following domains, subdomains or combinations thereof: a subdomain of domain III replacing a cleavage site of native TNFα; all of domain III; domain III with domain II or a subdomain thereof replacing a native TNFα cleavage site; domain III with domain I or a subdomain thereof replacing a native TNFα cleavage site; domain III with a subdomain of domain IV replacing a native TNFα cleavage site; domain III, domain II and domain I, or subdomains thereof. Preferably, the first nucleotide sequence encodes at least one domain or subdomain of one of the following TNF ligands: CD154, CD70, FasL and TRAIL. According to the invention, replacing a domain or subdomain containing a TNFα cleavage site with a domain or subdomain from one of these four other TNF ligands results in a chimeric TNFα that is markedly less susceptible to cleavage than native TNFα.

The first nucleotide sequence is operatively linked to a second nucleotide sequence that encodes an extracellular domain or subdomain of native TNFα involved in binding to TNFα receptors. This domain or subdomain comprises all of domain IV of native TNFα or a subdomain thereof that can bind TNF-R1, TNF-R2 or other TNFα receptors. In this way, the chimeric polynucleotide sequence provided by the present invention encodes a chimeric TNFα that binds to cells expressing a TNFα receptor.

Figure 2:
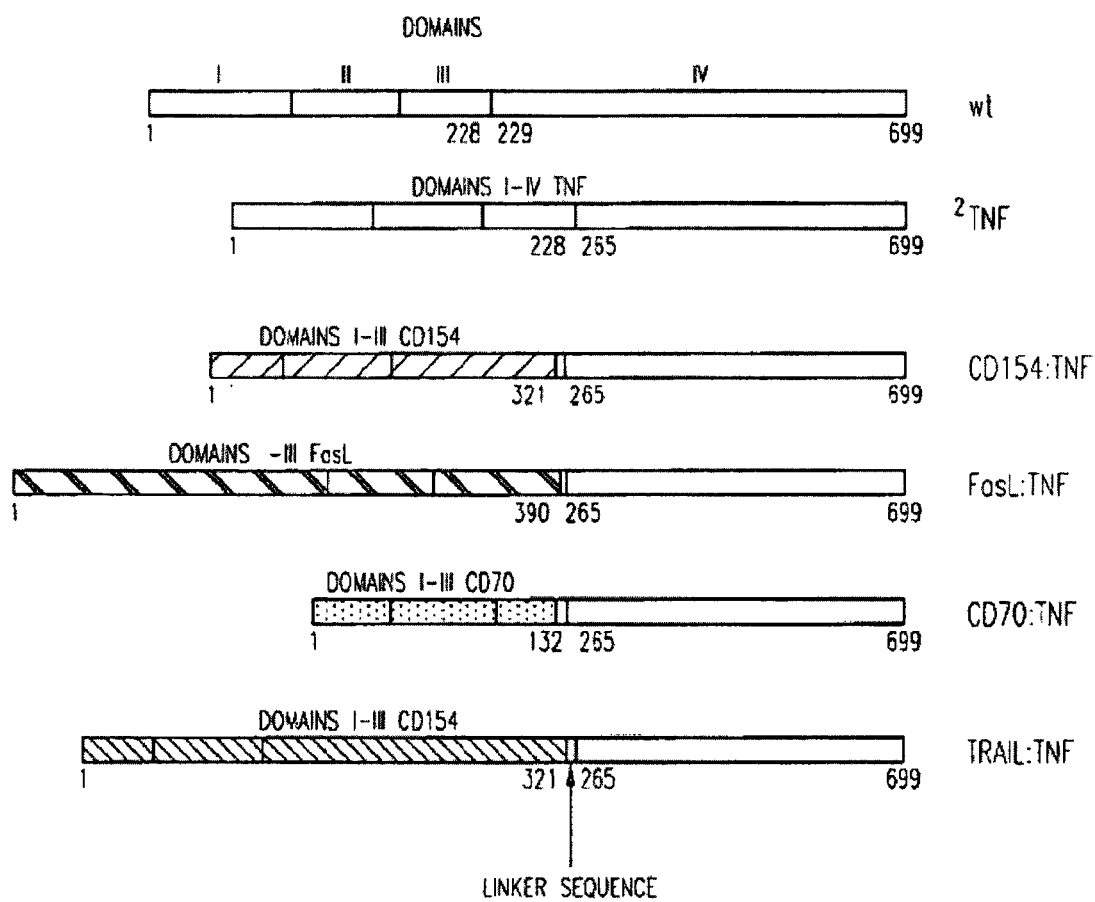
FIG. 2 is a schematic diagram of wild type TNFα (designated wt TNFα), a deletion mutant of TNFα (designated $^2$TNFα), and some exemplary TNFα chimeras of the present invention, depicting domains I-IV of those ligands and domain linkers.

A presently preferred polynucleotide sequence encodes a subdomain IV of native TNF& operatively linked to domain I, II and III of another ligand selected from the group consisting of CD154, CD70, FasL and TRAIL. For example, in one presently preferred embodiment, nucleotides encoding a domain IV or subdomain of domain IV of human TNFα is operatively linked to the nucleotides encoding domains I, II and subdomain III of human CD154 that also lacks the CD154 cleavage site (CD154:TNFα). Such a polynucleotide sequence is provided herein as SEQ. ID. NO. 1. Alternatively, the nucleotides encoding subdomain III of human CD154 may include the CD154 cleavage site (designated CD154+ mmp:TNFα). Another example of a presently preferred embodiment is a nucleotide sequence encoding a domain IV or a subdomain of domain IV of human TNFα operatively linked to nucleotide sequences encoding domains I, II, and III of human CD70 (SEQ. ID. NO. 2). SEQ. ID. NO. 3 provides yet another example of a presently preferred polynucleotide sequence, in which a nucleotide sequence encoding domain IV or a subdomain of domain IV of human TNFα is operatively linked to nucleotide sequences encoding domains I, II and III of human FasL. Finally, SEQ. ID. NO. 4, still another presently preferred embodiment of this invention, provides a nucleotide sequence encoding domain IV or a subdomain of domain IV of human TNFα operatively linked to nucleotide sequences encoding domains I, II and III of human TRAIL. In all of these embodiments, the nucleotides preferably encode subdomains of domain IV of human TNFα that lacks a TNFα cleavage site. In addition, domains I, II, and III of the TNF family members described in SEQ. ID. NO's. 1-4 are joined to domain IV of TNFα by a linker domain encoding a peptide from two to four amino acids. The presently most preferred polynucleotide sequence of the present invention is SEQ. ID. NO. 1. FIG. 2 shows domains I-IV of the above-described embodiments of chimeric TNFα. Moreover, the following Table II shows the nucleotide boundaries of these chimeric TNFα sequences.

TABLE II

| CONSTRUCT | DOMAINS I-III | DOMAIN IV OF TNF |
|---|---|---|
| CD154:TNFα | 1-321 | 265-699 |
| CD70:TNFα | 1-132 | 265-699 |
| FasL:TNFα | 1-390 | 265-699 |
| TRAIL:TNFα | 1-345 | 265-699 |
| CD154 + mmp:TNFα | 1-351 | 265-699 |

While the above polynucleotide sequences all comprise human TNF ligand *-sequences, the present invention also contemplates polynucleotide sequences from other species, such as, without limitation, murine polynucleotide sequences.

The encoded chimeric TNFα therefore comprise a polypeptide domain or subdomain of a TNF ligand other than TNFα that replaces a cleavage site of native TNFα. As a result, the chimeric TNFα is less susceptible to cleavage from the surface of cells than native TNFα. Preferably, the exchanged domain is taken from CD154, CD70, FasL or TRAIL. The preferred constructs are: domains I, II and subdomain III of human CD154 and a domain IV or a subdomain of domain IV of human TNFα (SEQ. ID. NO. 5); domains I, II and III of human CD70 and a domain IV or a subdomain of domain IV of human TNFα (SEQ. ID. NO. 6); domains I, II and III of human FasL and a domain IV or a subdomain of domain IV of human TNFα (SEQ. ID. NO. 7); and domains I, II and III of human TRAIL and a domain IV or a subdomain of domain IV of human TNFα (SEQ. ID. NO. 8). The presently most preferred embodiment for the chimeric TNFα of the present invention is SEQ. ID. NO. 5.

III. Genetic Constructs

The present invention also contemplates an expression vector or any other genetic construct that comprises a polynucleotide sequence of the present invention capable of expressing a chimeric TNFα in a target cell.

An expression vector useful in the present invention contains a polynucleotide sequence encoding a chimeric TNFα operatively linked to a suitable transcriptional or translational regulatory nucleotide sequence, such as one derived from a mammalian, microbial, viral, or insect gene. Such regulatory sequences include sequences having a regulatory role in gene expression, such as a transcriptional promoter or enhancer, an operator sequence to control transcription, a sequence encoding a ribosomal binding site within the messenger RNA, and appropriate sequences which control transcription, translation initiation, or transcription termination.

Particularly useful regulatory sequences include the promoter regions from various mammalian, viral, microbial, and insect genes. The promoter region directs an initiation of transcription through and including the polynucleotide sequence encoding the chimeric TNFα of the present invention. Useful promoter regions include the promoter found in the Rous Sarcoma Virus (RSV) long terminal repeat (LTR), human cytomegalovirus (CMV) enhancer/promoter region, lac promoters, promoters isolated from adenovirus, and any other promoter known by one of ordinary skill in the art would understand to be useful for gene expression in eukaryotes, prokaryotes, viruses, or microbial cells. Other promoters that are particularly useful for expressing genes and proteins within eukaryotic cells include mammalian cell promoter sequences and enhancer sequences such as those derived from polyoma virus, adenovirus, simian virus 40 (SV40), and the human cytomegalovirus. Particularly useful are the viral early and late promoters, which are typically found adjacent to the viral origin of replication in viruses such as the SV40. One of ordinary skill in the art will understand that the selection of a particular useful promoter depends on the exact cell lines and the other various parameters of the genetic construct to be used to express a polynucleotide sequence within a particular cell line.

Certain genetic constructs contemplated by the present invention therefore include a polynucleotide sequence operatively linked to either a promoter sequence or a promoter and enhancer sequence and also operatively linked to a polyadenylation sequence that directs the termination and polyadenylation of messenger RNA. Preferably, the polynucleotide sequence is constructed using the CMV promoter and the bovine growth hormone polyadenylation sequence.

IV. Host Cells

The present invention also contemplates various host cells that are transformed or transfected with an expression vector or other genetic construct that contains a polynucleotide sequence of the present invention. These cells may be prokaryotic or eukaryotic cells.

In some preferred embodiments the cells are normal antigen presenting cells of a mammal, such as monocytes, macrophages, B cells, and the like. In other preferred embodiments, the cells may be normal cells that are capable of stimulating bystander antigen presenting cells when a polynucleotide sequence of the present invention is introduced into these cells. The present invention also contemplates somatic cells that are not naturally capable of presenting antigen to the immune system but may be genetically engineered with the genes encoding the molecules required for antigen presentation, and thus allow these cells to act as artificial antigen presenting cells. A polynucleotide sequence encoding a chimeric TNFα may then be introduced into these artificial antigen presenting cells. Various tests are well known in the literature to determine whether a particular cell is able to function as an antigen presenting cell, such as cell proliferation or the production of lymphokines, and therefore this aspect of the present invention may be easily determined.

In addition to the above normal human cells, the present invention also contemplates introducing a polynucleotide sequence encoding a chimeric TNFα into various neoplastic or malignant cells, such as cells of the immune system and solid tumors. Such neoplastic cells that are contemplated include leukemia cells, such as acute monocytic leukemia (AML), acute myelomonocytic leukemia (AMML), chronic lymphocytic leukemia (CLL), chronic myelogenous or chronic myelomonocytic leukemia (CMML). Also contemplated are cells derived from lymphomas, gliomas, breast, cervical, ovarian, lung, bladder, or prostate cancers.

Finally, in a preferred embodiment of the present invention, a polynucleotide sequence encoding a chimeric TNFα is introduced into cells that express the cognate receptors for TNFα, such as TNF-R1 and TNF-R2, on surfaces of the cells.

V. Methods Utilizing Genetic Vectors and Constructs Containing an Accessory Molecule Ligand Gene Recognizing the interaction of TNFα and its cognate receptors in regulating the immune response, the present invention also contemplates methods of increasing the concentration of a membrane-stabilized ligand capable of binding to TNF-R1, TNF-R2, or some other cognate receptor for TNFα, by introducing a polynucleotide sequence encoding a chimeric TNFα into a cell, whereby the chimeric TNFα is less susceptible to cleavage from the surface of that cell relative to native TNFα. Because the chimeric TNFα is less susceptible to proteolytic cleavage, it has increased capacity to bind to its cognate receptor and induce either a cytolytic response or an immune response. In addition, the capacity of cells transfected with a polynucleotide sequence encoding a chimeric TNFα ligand of the present invention to induce apoptosis and clearance of cells bearing a TNFα receptor is increased.

The present invention is useful for any human cell that participates in an immune reaction either as a target for the immune system or as part of the immune system's response to the foreign target. The methods include ex vivo methods, in vivo methods, and various other methods that involve injection of polynucleotides or vectors into the host cell. The methods also include injection directly into the tumor or tumor bed.

The present invention thus contemplates ex vivo methods comprising isolation of cells from an animal or human subject. A polynucleotide sequence encoding a chimeric TNFα of the present invention is introduced into the isolated cells. The cells are then re-introduced at a specific site or directly into the circulation of the subject. In a preferred embodiment of the present invention, cell surface markers, including molecules such as tumor markers or antigens that identify the cells, may be used to specifically isolate these cells from the subject.

The present invention also contemplates introducing a polynucleotide sequence encoding a chimeric TNFα into the desired cells within the body of an animal or human subject without first removing those cells from the subject. Methods for introducing polynucleotide sequences into specific cells in vivo, or within the subject's body are well known and include use of expression vectors and direct injection of various genetic constructs into the subject. In a typical application, an expression vector containing a polynucleotide sequence of the present invention is introduced into the circulation or at a localized site of the subject to allow the vector to specifically infect the desired cells. In other preferred embodiments the vector is injected directly into the tumor bed present in a subject that contains at least some of the cells into which the polynucleotide sequence of the present invention is to be introduced.

The present invention also contemplates directly injecting into an animal or human subject a genetic construct that includes a polynucleotide sequence encoding a chimeric TNFα, and may additionally include a promoter and a polyadenylation sequence. Examples of such useful methods have been described (Vile et al, Ann Oncol, 5:59-65, 1994). The genetic construct may also be directly injected into the muscle or other sites of an animal or human subject or directly into the tumor or tumor bed of the subject.

VI. Methods of Treating Neoplasia

The present invention is also directed to gene transfer of a polynucleotide sequence encoding a chimeric TNFα of the present invention to induce apoptosis of tumor cells. In addition to directly causing apoptosis of these tumors through interactions between TNFα and its receptors TNF-R1 and TNF-R2, the present invention also contemplates infecting tumor cells with a chimeric TNFα so that the ligand is expressed in a membrane-stabilized manner and thereby may also participate in the immune response.

Thus, the present invention contemplates methods of treating neoplasia, comprising inserting into a neoplastic cell a polynucleotide sequence of the present invention, so that the encoded chimeric TNFα is expressed on the surface of the neoplastic cells. The present invention contemplates treating human neoplasia both in vivo and ex vivo.

In a preferred method of treating neoplasia, the method further comprises the steps of first obtaining the neoplastic cells from a subject, inserting therein a polynucleotide sequence of the present invention so that a chimeric TNFα is expressed on the surface of the neoplastic cells, and re-administering the cells back into the subject. One of ordinary skill in the art will understand that numerous methods are applicable for re-administering the transformed neoplastic cells into the subject.

Examples

I. Construction of a Genetic Construct and Gene Therapy Vector Containing a Chimeric Accessory Molecule Ligand Gene The chimeric accessory molecule ligand genes of SEQ ID NO. 1-SEQ ID NO. 4 were constructed and cloned as follows:

i. Preparation of Chimeric Accessory Molecule Ligand Gene Utilizing Domains from Two Different Accessory Molecule Ligand Genes DNA fragments encoding domains I-III of a ligand (CD154, CD70, FasL, and TRAIL) were amplified from the full-length cDNA template by PCR using oligonucleotide primers specific for 5' and 3' regions flanking domain I-III of the ligand. In addition, a DNA fragment encoding subdomain IV of TNFα was PCR amplified. A BamHI restriction endonuclease site was engineered into the domain III-IV junction PCR primer set to enable ligation of the domain I-III fragment with domain IV fragment. In addition, restriction endonuclease sites were added to the 5' and 3' primers that flank domains I and IV, respectively, allowing for ligation into the pcDNA3 vector. Following PCR amplification of the domain I-III fragment and the domain IV fragment, the DNA fragments were digested with BamHI and restriction enzyme corresponding to the 5' or 3' flanking regions of domains I and IV. Following digestion, the domain fragment and domain IV fragment were ligated at the BamHI site in parallel to ligation into the multiple cloning site of the eukaryotic expression plasmid pcDNA3 (Invitrogen, San Diego, Calif.). The chimeric TNFα (hereinafter in the examples, TNFα will be referred to simply as "TNF") DNA insert was flanked by the strong-heterologous CMV promoter and the bovine growth hormone polyadenylation sequence.

ii. Adenovirus Synthesis

The chimeric TNF-pcDNA3 plasmids were digested with the restriction enzymes NruI and Sma I to release a DNA fragment containing the CMV promoter from pCDNA3, the chimeric TNF gene, and the polyadenylation signal from pCDNA3. Following gel purification of this fragment by separation of the digested DNA on a 1% agarose gel, the DNA fragment was ligated into the EcoRV site of the adenoviral shuttle vector MCS (SK) pXCX2. This plasmid is a modification of the plasmid pXCX2 such that the pBluescript polylinker sequence has been cloned into the E1 region, U. R. Tozer, UCSD, unpublished data, September 1993). Following purification of chimeric TNF-MCS (SK) pXCX2 plasmid, 5 ug of this shuttle plasmid was cotransfected with 5 ug of JM17 plasmid into 293AC2 cells using the calcium phosphate Profection Kit from Promega according to the manufacturer's instructions. Following transfection, the cells were cultured for 5 days to allow for homologous recombination and viral synthesis. Total cells and supernatant were then harvested and freeze-thawed thrice to release cell-associated adenovirus.

Following the initial viral production, a clonal isolate of the virus obtained by plaque purification. Briefly, the freeze-thawed viral supernatant was cleared of debris by centrifugation at 1000 rpm in a tabletop centrifuge for 5 minutes. 293AC2 cells grown to confluency in 6 well tissue culture plates were then infected with serial dilutions of the viral supernatant for 1-2 hours. Following infection, the media was aspirated and cells overlayed with DMEM media containing 4% fetal calf serum and 0.65% agarose held at 56.degree. C. Following 4-6 days incubation, isolated plaques were picked into 1 ml of media and subsequently used for viral amplification.

Large-scale adenovirus preparations were prepared by successively infecting increasing quantities of 293AC2. Purified adenovirus was then purified over cesium chloride step gradients. This method makes use of a cesium chloride gradient for concentrating virus particles via a step gradient, with the densities of 1.45 g/cm.sup.3 and 1.20 g/cm.sup.3, in which 293AC2 expanded virus samples are centrifuged for 2 hours in a SW40 rotor (Beckman, Brea, Calif.) at 25,000 rpm at 4.degree. C. The virus band was isolated using a 27-gauge needle and syringe and desalted using a Sephadex G-25 DNA grade column (Pharmacia, Piscataway, N.J.). The virus was desalted against phosphate-buffered saline containing 10% glycerol and stored at −70.degree. C. The final titer of the virus was determined by anion-exchange HPLC.

II. Introduction and Expression of a Chimeric Accessory Molecule Ligand Gene in CLL Cells and HeLa Cells i. Expression TNFα surface expression was detected by flow cytometry. Briefly, the adherent cells were detached from the wells aspiration of the media and addition of detaching solution (PBS containing 10 mM EDTA, pH 8). Once the cells detached from the plate, half of each sample was analyzed for ligand expression by flow cytometry. Briefly, cells were washed once in FACS staining buffer (composed of PBS containing 3% FCS and 0.05% sodium azide), resuspended in FACS buffer to approximately 10.sup.7 cells/ml, and 5.times.10.sup.5 (50 ul) cells were plated in 96-well u-bottom plastic microwell plates. For human TNFα specific staining, PE-conjugated antibody specific for TNFα (Pharmingen) was added for 30 minutes at 4.degree. C. The cells were then washed twice with FACS buffer, resuspended in FACS buffer, and transferred to FACS tubes for data acquisition. To control for nonspecific antibody binding, all samples were stained with appropriate isotype control antibodies. Furthermore, dead cells and debris were excluded from analysis by addition of long/ml propidium iodide to all staining reactions. The cells were analyzed by flow cytometry for TNFα expression using a FACSCaliber flow cytometer (Becton Dickinson).

Figure 3:
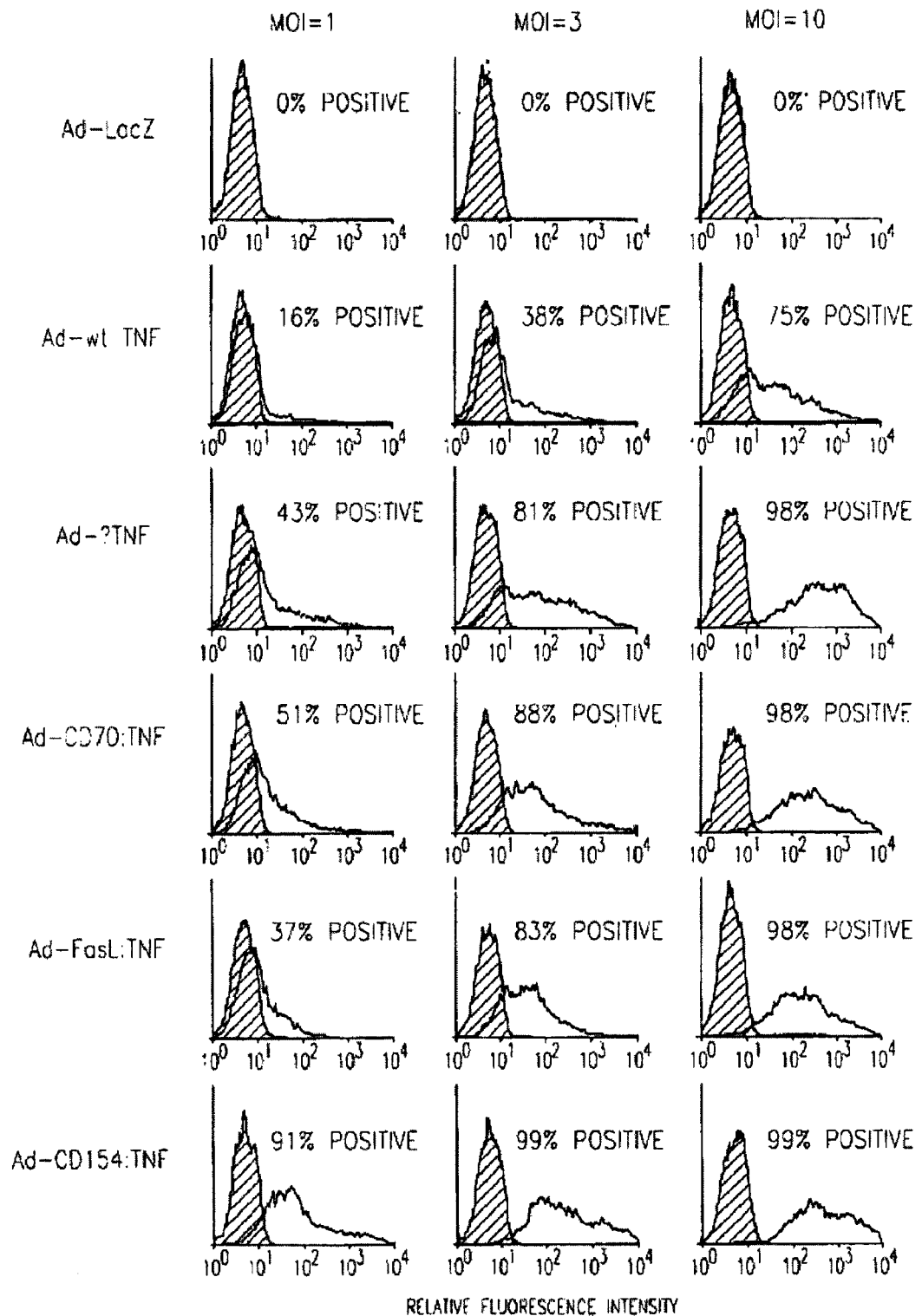
FIG. 3 is a series of fluorescent activated cell sorting (FACS) histograms showing the comparative surface expression of wt TNFα, the deletion mutant $^2$TNFα, and some exemplary TNFα chimeras of the present invention on HT1080 cells. The shaded areas represent the background fluorescent staining with isotype-control antibody. The unshaded areas represent the expression level of wt TNFα, the previously described membrane-stabilized $^2$TNFα, and exemplary chimeric TNFα ligands on the surface of HT1080 cells infected with adenovirus encoding the DNA sequences.

(FIG. 3) shows the expression of different chimeric TNF constructs compared to wild type TNF and a previously described membrane-stabilized TNF (designated TNF) following adenovirus infection of HT1080 cells. Briefly, HT1080 cells were infected with increasing titers of adenovirus, indicated above histogram columns. Two days following infection, cells were analyzed for TNF surface expression by flow cytometry. This data shows the adenovirus vectors encoding the chimeric TNF constructs were expressed on the cell surface as detected using a fluorochrome-conjugated antibody specific for TNF. In addition, this data shows there were differences in the surface expression levels between TNF constructs. Specifically, Ad-CD154:TNF infection resulted in the highest levels of surface expression of TNF. Similar patterns of expression were obtained in a panel of other cell lines, including 293, HeLa, COLO205, A549, HCT15, PC3, RPM18226, and BT20 suggesting the differences in expression between the TNF constructs are not cell type restricted.

Figure 4:
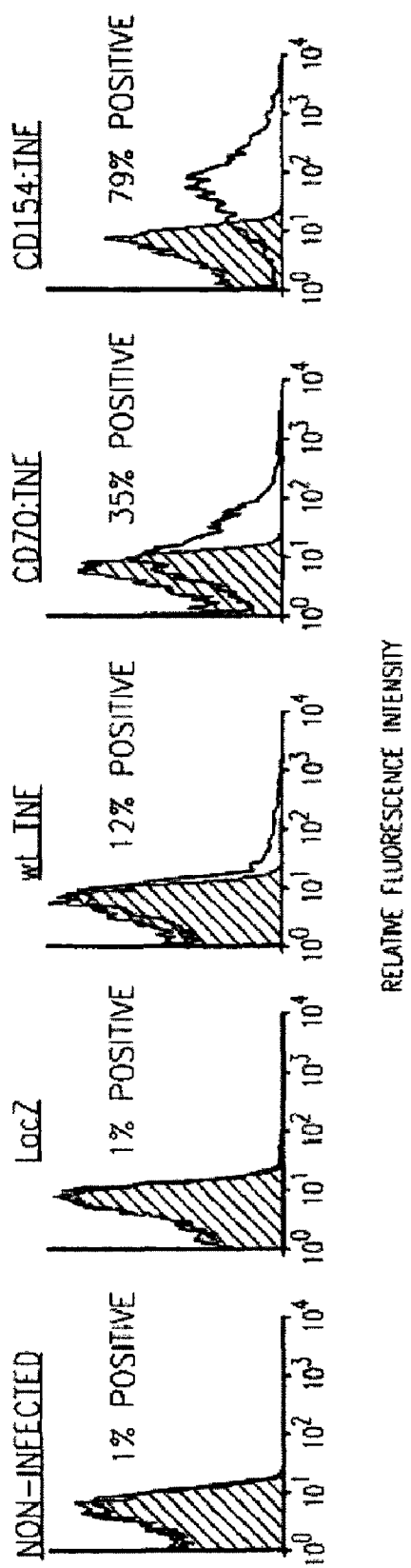
FIG. 4 is a series of FACS histograms showing the comparative surface expression of TNFα by uninfected CLL B cells and cells infected with adenovirus encoding wt TNFα and some exemplary TNFα chimeras of the present invention. The shaded areas represent the background fluorescence of isotype-control stained cells. The unshaded areas represent the expression of human TNFα on cells stained with TNF-specific antibody.

(FIG. 4) shows the expression of different chimeric TNF constructs following adenovirus infection of chronic lymphocytic leukemia (CLL) B cells. CLL cells were infected with adenovirus, as indicated above each histogram, at a multiplicity of infection (M.O.I.) ratio of 1000. Two days following infection, CD19.sup.+ B cells were examined for TNF surface expression by flow cytometry. In addition, the figure shows the same pattern of expression differences between TNF constructs that we observed for cell lines described above. Namely, TNF chimera expression was greater than wild type TNF. Again, the greatest TNF surface expression was obtained with the hCD154:TNF chimera.

ii. Generation of Soluble Molecules

Figure 5:
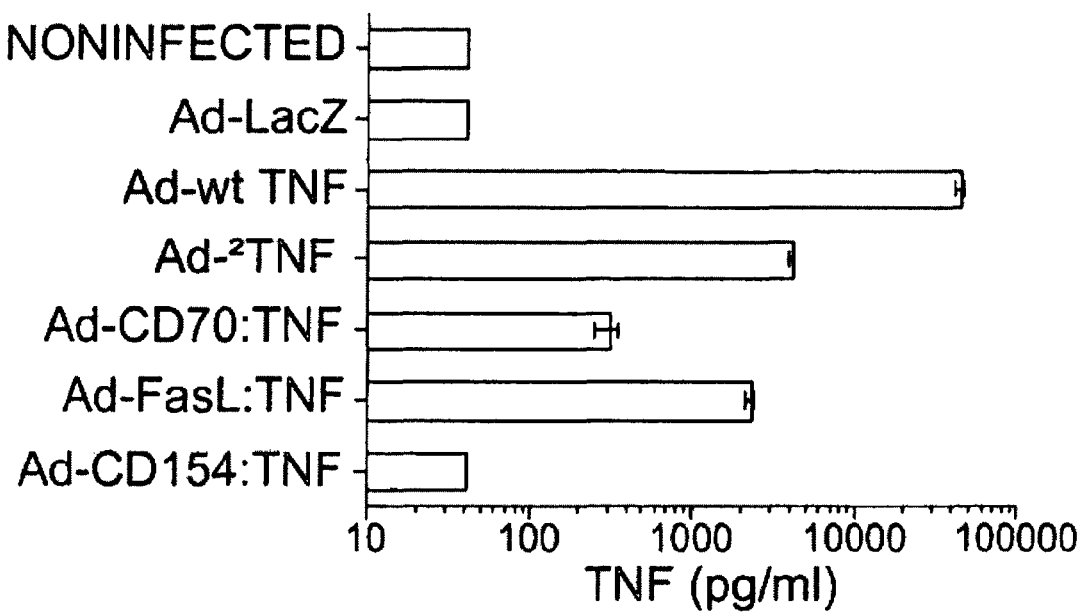
FIG. 5 shows the quantity of soluble TNFα generated by HT1080 cells infected with wt TNFα adenovirus, $^2$TNFα adenovirus, and exemplary chimeric TNFα adenovirus vectors, as measured by a TNF-specific ELISA assay.

2. Soluble TNF Generation: ELISA Quantitation (FIG. 5) shows the quantity of soluble TNF generated by HT1080 cells infected with chimeric TNFα adenovirus vectors. Cells were infected at a M.O.I. ratio of 10. Two days following infection, supernatant was harvested and cleared of dead cells and debris by centrifugation. Soluble TNF was measured by enzyme linked immunosorbent assay (ELISA) using a TNF-specific ELISA assay from Pharmingen, Inc. (La Jolla, Calif.) according to the manufacturer's instructions. Specific quantities of TNF were calculated based on titrations of a known quantity of recombinant TNF (Biosource International). This data shows the chimeric TNF constructs generated significantly less soluble TNF than either wild type TNF (wt TNF), or the previously described membrane-stabilized TNF lacking the putative mmp proteolytic site. Moreover, despite the highest surface expression levels of CD154:TNF compared to all other constructs, CD154:TNF generates the least soluble TNF. This pattern of soluble TNF release was also observed for other cell lines, including HeLa, 293, A549, COLO205, HCT-15, and BT-20.

iii. Functional Assays of Chimeric Accessory Molecule Ligands

Figure 6:
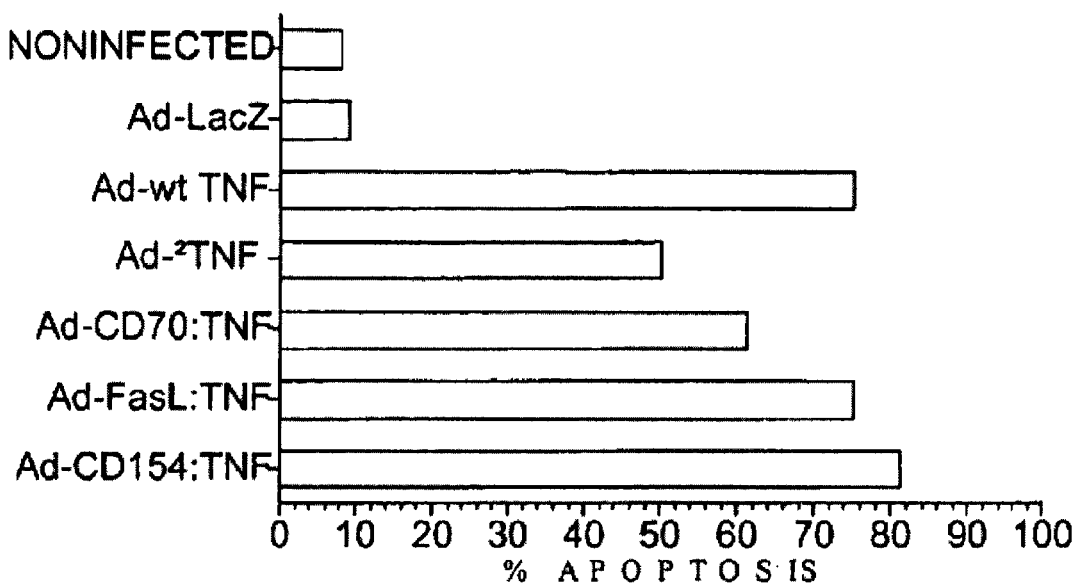
FIG. 6 is a graph representing cell death of WEHI164 cells following infection with adenovirus encoding wt TNFα, ²TNFα, and exemplary chimeric TNFα adenovirus vectors.

1. TNF Chimera Killing of WEHI164 Fibrosarcoma Cells: Coculture Assay (FIG. 6) demonstrates TNF chimeras are functional using a biological apoptosis assay previously described (Espevik et al, J Immunol Methods, 95:99-105, 1986). Following infection of HeLa cells with adenovirus for two days at a M.O.I. ratio of 10, WEHI164 cells, a TNF sensitive cell line, were overlayed on the infected HeLa cells and incubated an additional 18 hr. The WEHI164 cells were prelabelled with PKH26 (Sigma, Inc.), a red fluorescent chemical that enables gating the WEHI164 cells from the HeLa cells. WEHI cells were stained with propidium iodide and analyzed for cell death by flow cytometry. This data shows that WEHI cells were killed following coculture with TNF-expressing HeLa cells.

Figure 7:
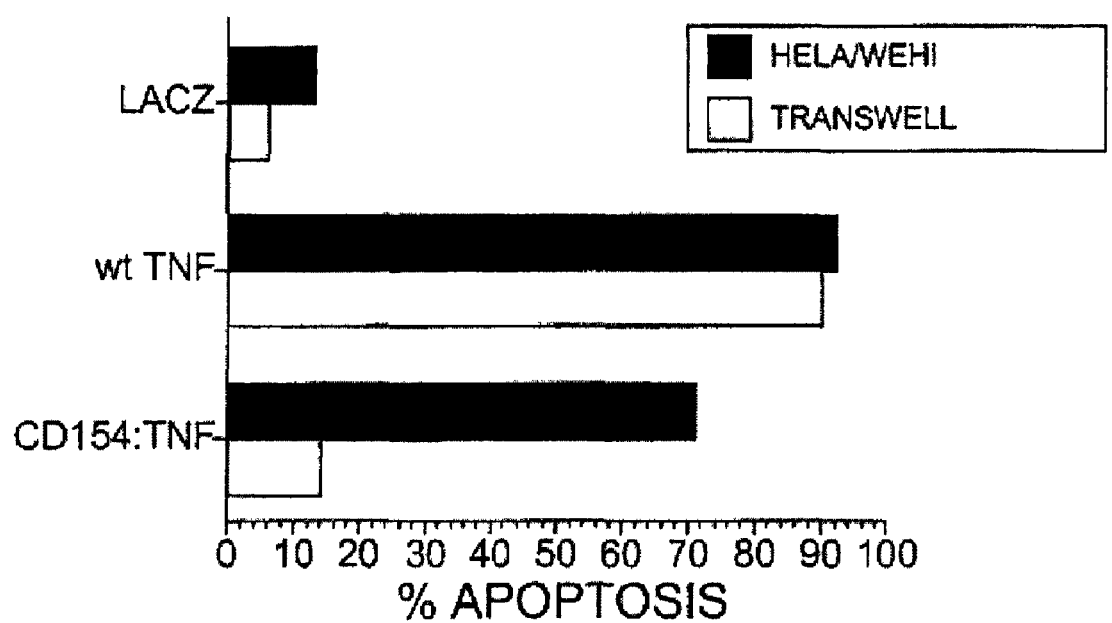
FIG. 7 is a diagram showing apoptosis of WEHI164 cells following coincubation with HeLa cells infected with adenovirus encoding CD154:TNFα chimera compared to cells infected with wt TNFα. The darker bar represents apoptosis through cell-to-cell contact, while the lighter bar represents apoptosis mediated by the action of the soluble form of TNFα.

2. Cell Contact Dependent Apoptosis of WEHI164 by TNF Chimera (FIG. 7) demonstrates contact dependent killing of WEHI164 cells by TNF chimera. This demonstrates membrane-stabile expression of the TNF chimera. Briefly, HeLa cells were infected with adenovirus for one day at a M.O.I. ratio of 10. WEHI164 cells were then mixed directly with the infected HeLa cells or separated from the HeLa cells by a 0.2 micron transwell insert. This insert prevents direct cell-cell contact but permits diffusion of soluble molecules (e.g. soluble TNF) between cells. 18 hr following mixing, the WEHI164 cells were analyzed for apoptosis as described in FIG. 6. In contrast to wt TNF that released soluble TNF that could kill WEHI164 cells separated by the transwell insert, the TNF chimera did not release soluble TNF that could similarly induce apoptosis.

Figure 8:
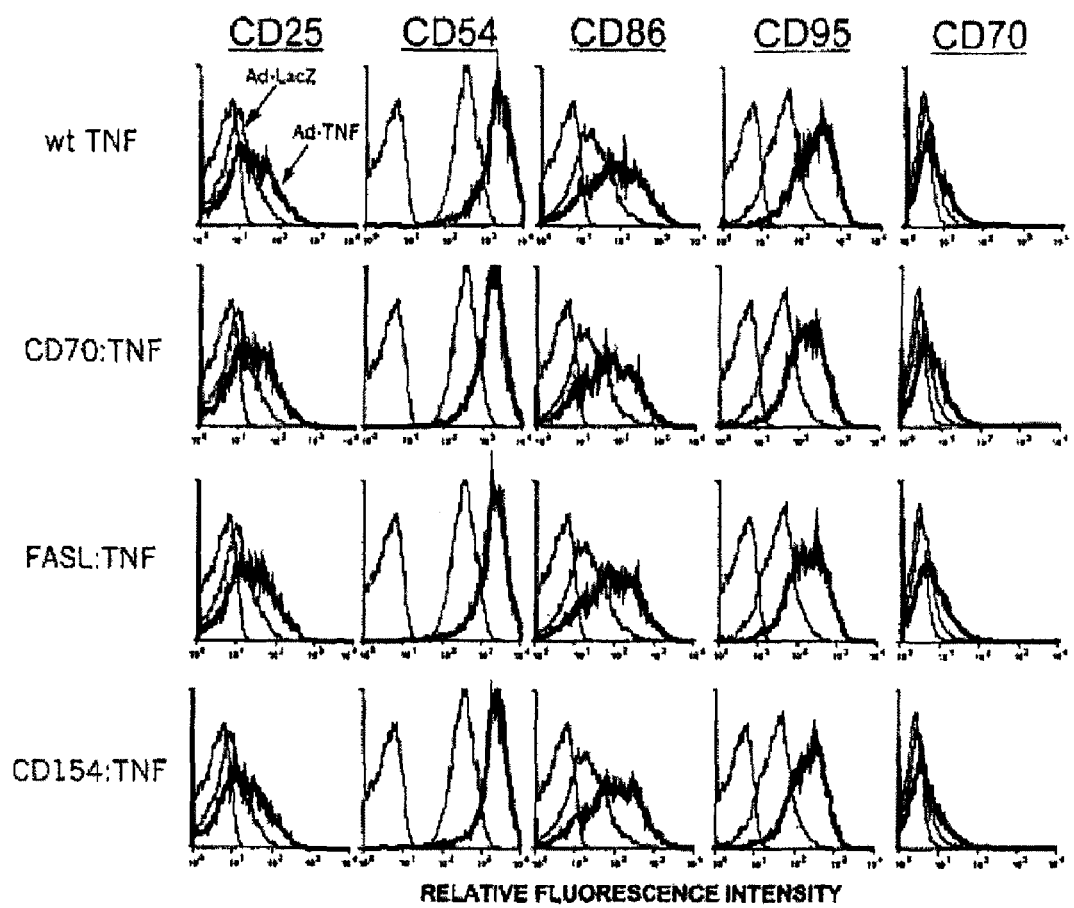
FIG. 8 is a series of FACS histograms showing the comparative surface expression of phenotypic markers CD25, CD54, CD96, CD95, and CD70 by CLL B cells following co-culture with HeLa cells expressing wt TNFα and exemplary chimeric TNFα constructs of the present invention.

3. TNF Chimera Activation of CLL B Cells (FIG. 8) shows the activation of CLL B cells cocultured with HeLa cells expressing chimeric TNF. HeLa cells were infected with adenovirus at a M.O.I ratio of 10. Two days following infection, CLL cells were overlayed on the HeLa cells and co-incubated for 1 day. CD19.sup.+ CLL cells were then analyzed for changes in expression of phenotypic markers (CD25, CD54, CD86, CD95, and CD70). Bold-line histograms represent CLL cells cocultured with Ad-TNF vector, as labeled to the left of each row. Thin-line histograms represent coculture with Ad-LacZ virus. Shaded histograms represent staining with an isotype control monoclonal antibody of irrelevant specificity. This data shows that chimeric TNF constructs are functional in that they modulated expression of a panel of phenotypic markers on CLL cells characteristic of lymphocyte activation.

Figure 9:
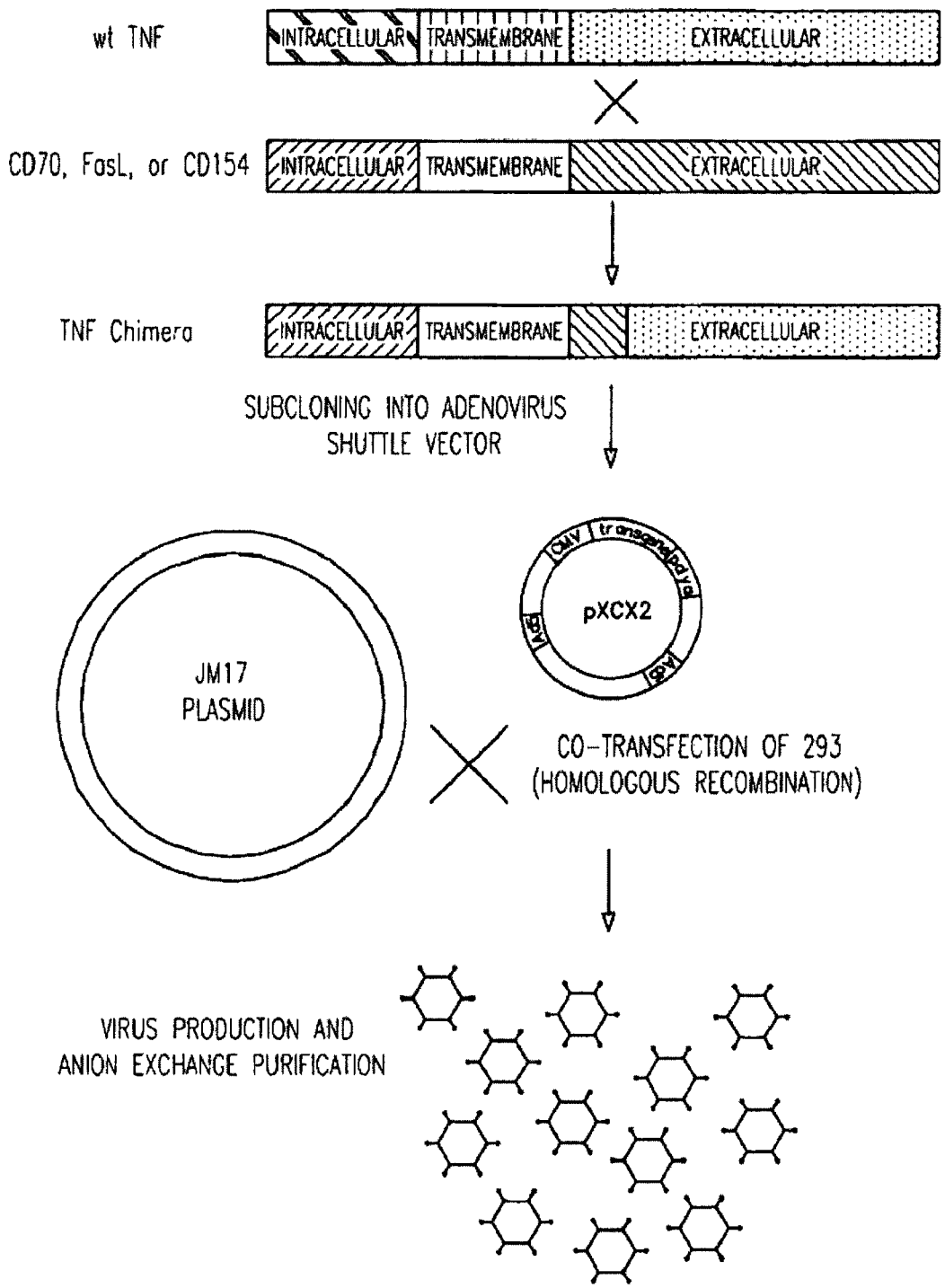
FIG. 9 shows the quantity of soluble TNFα generated by HeLa cells infected with adenovirus vectors encoding wt TNFα, CD154:TNFα chimera, CD154:TNFα containing a putative CD154 mmp recognition sequence at the chimera junction site, or CD154:TNFα lacking the linker domain at the chimera junction site.

4. Modified mmp Site TNF Chimera Soluble TNF Generation (FIG. 9) shows the quantity of soluble TNF generated by HeLa cells infected with chimeric CD154:TNFα adenovirus vector containing the putative CD154 mmp recognition site that is absent from the CD154:TNF chimera described in FIGS. 3-8. This construct is termed CD154+mmp:TNF (SEQUENCE ID#9). Cells were infected with adenovirus at a M.O.I. ratio of 10. Two days following infection, supernatant was harvested and cleared of dead cells and debris by centrifugation. Soluble TNF was measured by enzyme linked immunosorbent assay (ELISA) using a TNF-specific ELISA assay from Pharmingen, Inc. (La Jolla, Calif.) according to the manufacturer's instructions. Specific quantities of TNF were calculated based on titrations of a known quantity of recombinant TNF (Biosource International). This data shows the modifications described above to the original CD154:TNF chimera did not affect their susceptibility to proteolytic cleavage into a soluble molecule.

Figure 10:
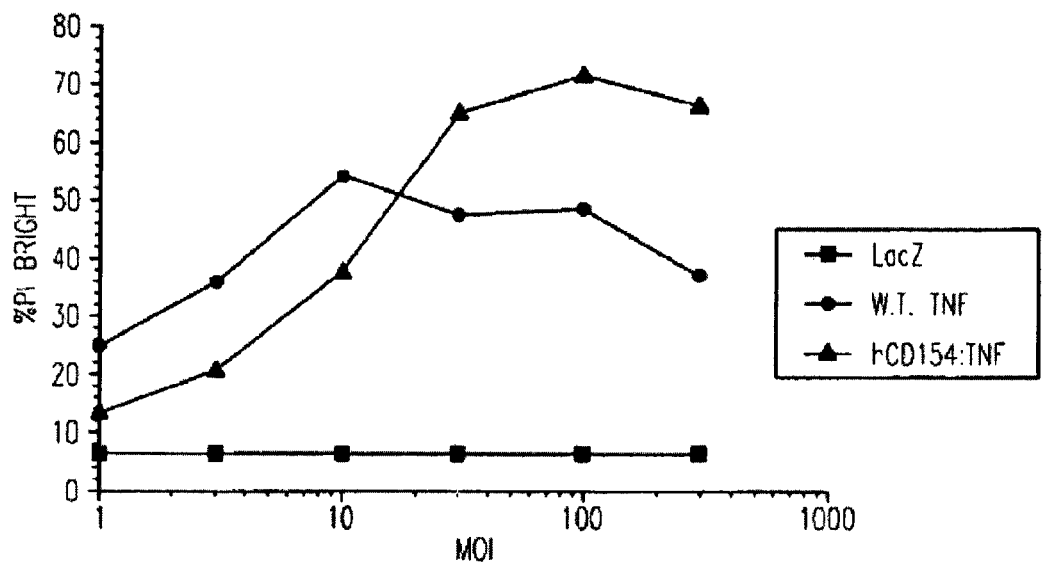
FIG. 10 shows the quantity of soluble TNFα generated by HeLa cells transfected with plasmids encoding CD70:TNFα chimeras with various modifications made to the linker domain.

5. Modified Linker Domain Effect on Soluble TNF Generation (FIG. 10) shows the quantity of soluble TNF generated by HeLa cells transfected with plasmids encoding CD70:TNF chimeras with various modifications made to the linker domain. In addition to the CD70:TNF construct described in FIGS. 3-4, constructs with a truncated linker domain (Linker CD70:TNF, Sequence ID#10) and with a linker domain containing a modified amino acid sequence (Linker.sup.DP.fw-darw.GA CD70:TNF, Sequence I D#11) are shown. HeLa cells were transfected with plasmid using Lipofectamine2000 (Gibco-BRL) according to the manufacturer's instructions. Two days following transfection, supernatant was harvested and soluble TNF was measured by ELISA as described above. This data shows that modifications to the linker domain of TNF chimeras do not affect the stability of these constructs.

Figure 11:
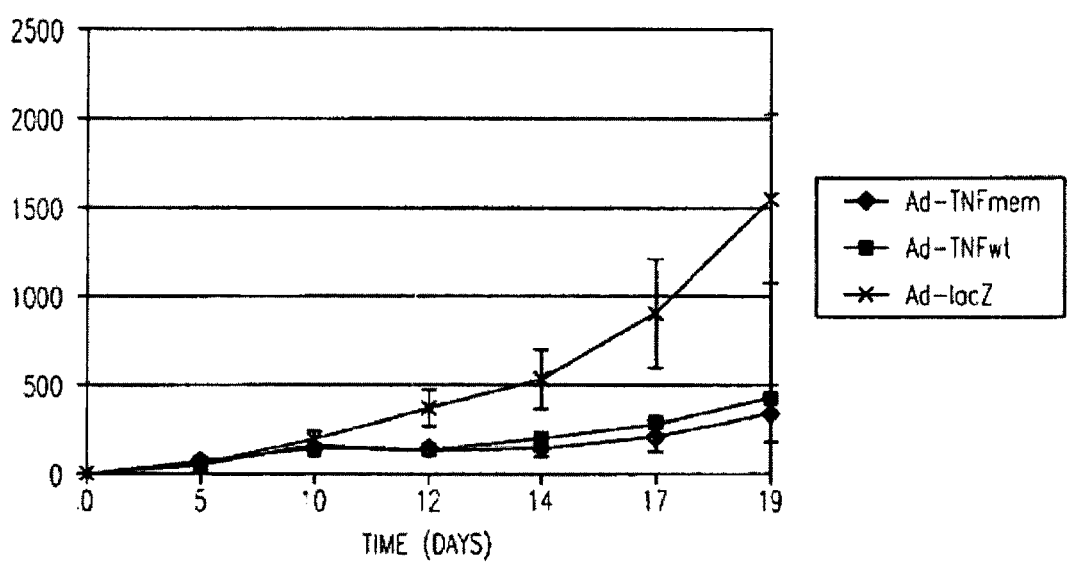
FIG. 11 shows the percent of tumor bearing mice over time following injection of pre-established tumors with either control adenovirus (LacZ), wt TNFα encoding adenovirus, or CD154:TNFα chimera encoding adenovirus.

6. Treatment of Pre-Established Murine WEHI164 Tumors with Chimeric INF (FIG. 11) shows the percent of tumor bearing mice with pre-established WEHI164 tumors following intratumoral injection with adenovirus encoding either .beta.-galactosidase (LacZ), wt TNF, or chimeric CD154:TNF. Briefly, Balb/c mice were inoculated subcutaneously with 3.times.10.sup.6 WEHI164 cells and tumor nodules were allowed to form for 10 days. On days 10, 12, and 14 following tumor inoculation, 5.times.10.sup.8 plaque forming units (pfu) of virus was delivered by intra-tumoral injection. Animals were then monitored weekly for tumor presence. Animals were euthanized when the tumor diameter reached >2 cm. This data shows the 75% of mice treated with chimeric CD154:TNF had complete tumor regression, compared to tumor regression in only 50% of mice treated with wt TNF. There was no tumor regression in mice treated with control adenovirus (Ad-LacZ). This data suggests chimeric TNF is therapeutically active against tumors and this activity is greater than wt TNF.

While preferred embodiments have been shown and described, it will be apparent to one of ordinary skill in the art that numerous alterations may be made without departing from the spirit or scope of the invention. The invention is not to be limited except in accordance to the following claims and their legal equivalents.

What is claimed is:

1. A nucleic acid molecule encoding a chimeric TNFα ligand polypeptide, comprising a first polynucleotide encoding Domain III of FasL, and a second polynucleotide encoding Domain IV of TNFα protein lacking a metalloproteinase recognition site between Val77 and Pro88 of Domain IV of the wild-type TNFα molecule, wherein the Domain IV fragment binds to TNFα receptor.

2. The nucleic acid molecule of claim 1, further comprising a third polynucleotide that encodes Domain II of FasL.

3. The nucleic acid molecule of claim 2, further comprising a fourth polynucleotide that encodes Domain I of FasL.

4. A nucleic acid molecule encoding a chimeric TNFα ligand polypeptide, comprising a first polynucleotide encoding Domain III of CD70, and a second polynucleotide encoding Domain IV of TNFα protein lacking a metalloproteinase recognition site between Val77 and Pro88 of Domain IV of the wild-type TNFα molecule, wherein the Domain IV fragment binds to TNFα receptor.

5. The nucleic acid molecule of claim 4, further comprising a third polynucleotide that encodes Domain II of CD70.

6. The nucleic acid molecule of claims 5, further comprising a fourth polynucleotide that encodes Domain I of CD70.

7. The nucleic acid molecule of claim 1, wherein the encoded chimeric molecule is less resistant to cleavage from a cell membrane into soluble form than is native TNFα in HeLa cells.

8. The nucleic acid molecule of claim 4, wherein the encoded chimeric molecule is less resistant to cleavage from a cell membrane into soluble form than is native TNFα in HeLa cells.

9. A chimeric TNFα ligand polypeptide, comprising Domain III of FasL, and Domain IV of TNFα protein lacking a metalloproteinase cleavage site present in Domain IV of the wild-type TNFα molecule, wherein the Domain IV fragment binds to TNFα receptor.

10. The chimeric TNFα of claim 9, further comprising a linker domain encoding a peptide of at least one amino acid that links the Domain III fragment to the Domain IV fragment.

11. A chimeric TNFα ligand polypeptide, comprising Domain III fragment of CD70, and Domain IV of TNFα protein lacking a metalloproteinase cleavage site present in Domain IV of the wild-type TNFα molecule, wherein the Domain IV fragment binds to TNFα receptor.

12. The chimeric TNFα of claim 11, further comprising a linker domain encoding a peptide of at least one amino acid that links the Domain III fragment to the Domain IV fragment.

13. An expression vector, comprising the nucleic acid molecule of claim 1.

14. The expression vector of claim 13, further comprising viral DNA or bacterial DNA.

15. The expression vector of claim 14, wherein said viral DNA is selected from the group consisting of adenoviral DNA, retroviral DNA or adeno-associated viral DNA.

16. An expression vector, comprising the nucleic acid molecule of claim 4.

17. The expression vector of claim 16, further comprising viral DNA or bacterial DNA.

18. The expression vector of claim 17, wherein said viral DNA is selected from the group consisting of adenoviral DNA, adeno-associated viral DNA or retroviral DNA.

19. A genetic construct comprising the nucleic acid molecule according to claim 1 operatively linked to a promoter sequence and to a polyadenylation signal sequence.

20. A genetic construct comprising the nucleic acid molecule according to claim 3 operatively linked to a promoter sequence and to a polyadenylation signal sequence.

21. A host cell, comprising an expression vector according to claim 13.

22. The host cell of claim 21, wherein the cell is a mammalian cell, tumour cell or antigen presenting cell.

23. A host cell, comprising a genetic construct according to claim 19 or 20.

24. The host cell of claim 23, wherein the cell is a mammalian cell, tumour cell or antigen presenting cell.

25. A process for producing a chimeric TNFα polypeptide comprising culturing a host cell of claim 21 under conditions suitable to effect expression of the protein.

26. A process for producing a chimeric TNFα polypeptide comprising culturing a host cell of claim 23 under conditions suitable to effect expression of the protein.

* * * * *